United States Patent
Yamada et al.

(10) Patent No.: US 9,492,309 B2
(45) Date of Patent: Nov. 15, 2016

(54) NASAL CAVITY INSERTION DEVICE

(75) Inventors: Hiroshi Yamada, Otsu (JP); Yosuke Taniguchi, Otsu (JP); Yoshiki Hattori, Otsu (JP); Kenji Hioki, Otsu (JP); Kae Fujiwara, Otsu (JP)

(73) Assignee: seven dreamers laboratories, Inc., Tokyo (JP)

( * ) Notice: Subject to any disclaimer, the term of this patent is extended or adjusted under 35 U.S.C. 154(b) by 104 days.

(21) Appl. No.: 13/582,213

(22) PCT Filed: Mar. 1, 2011

(86) PCT No.: PCT/JP2011/001181
§ 371 (c)(1),
(2), (4) Date: Aug. 31, 2012

(87) PCT Pub. No.: WO2011/108253
PCT Pub. Date: Sep. 9, 2011

(65) Prior Publication Data
US 2012/0318279 A1 Dec. 20, 2012

(30) Foreign Application Priority Data

Mar. 5, 2010 (JP) .................. 2010-049338
Sep. 3, 2010 (JP) .................. 2010-197663

(51) Int. Cl.
*A61F 5/56* (2006.01)
*A61M 16/04* (2006.01)
*A61F 2/94* (2013.01)

(52) U.S. Cl.
CPC . *A61F 5/56* (2013.01); *A61F 2/94* (2013.01); *A61M 16/0406* (2014.02); *A61M 16/0461* (2013.01)

(58) Field of Classification Search
USPC ......... 128/848, 858, 206.11, 207.18, 201.18, 128/201.23, 204.12; 606/191–192, 196, 606/199–202
See application file for complete search history.

(56) References Cited

U.S. PATENT DOCUMENTS

| 1,256,188 | A | * | 2/1918 | Wilson .................... 606/199 |
| 2,693,799 | A | * | 11/1954 | Herman, Jr. ............. 128/201.18 |
| 5,571,135 | A | | 11/1996 | Fraser et al. |
| 5,603,698 | A | | 2/1997 | Roberts et al. |
| 5,662,713 | A | | 9/1997 | Anderson et al. |
| 6,328,753 | B1 | | 12/2001 | Zammit |
| 6,494,205 | B1 | * | 12/2002 | Brown .................... 128/206.11 |

(Continued)

FOREIGN PATENT DOCUMENTS

| FR | 2631229 | 11/1989 |
| JP | H09-503945 A | 4/1997 |

(Continued)

OTHER PUBLICATIONS

International Search Report for PCT/JP2011/001181 dated Apr. 5, 2011.

(Continued)

*Primary Examiner* — Ophelia A Hawthorne
(74) *Attorney, Agent, or Firm* — Hamre, Schumann, Mueller & Larson, P.C.

(57) ABSTRACT

A nasal cavity insertion device is provided that includes a tubular main body part, at least one elastically deforming part disposed on the outer peripheral surface of the tubular main body part, and a water soluble holding part. The water soluble holding part holds the elastically deforming part in a diameter-reduced state.

8 Claims, 21 Drawing Sheets

(56) References Cited

U.S. PATENT DOCUMENTS

| | | | |
|---|---|---|---|
| 6,564,800 B1 | 5/2003 | Olivares | |
| 8,133,276 B2* | 3/2012 | Saidi | 623/10 |
| 2006/0085027 A1* | 4/2006 | Santin et al. | 606/199 |
| 2006/0235457 A1 | 10/2006 | Belson | |
| 2007/0191876 A1 | 8/2007 | Dubrul et al. | |
| 2008/0053458 A1 | 3/2008 | De Silva et al. | |
| 2009/0266365 A1* | 10/2009 | Oberle | A61F 5/56 128/207.18 |
| 2011/0125091 A1* | 5/2011 | Abbate | A61F 2/186 604/96.01 |

FOREIGN PATENT DOCUMENTS

| | | |
|---|---|---|
| JP | 2006-204630 | 8/2006 |
| JP | 2010-154919 A | 11/2008 |
| JP | 2009-034384 | 2/2009 |
| JP | 2009-072581 | 4/2009 |
| JP | 2009-072582 | 4/2009 |
| JP | 2008-538709 A | 7/2010 |

OTHER PUBLICATIONS

Chinese Office Action dated Aug. 22, 2014, issued in corresponding Chinese application.

European Search Report dated Jul. 18, 2014, issued in corresponding European application.

* cited by examiner

Sc ⟵ ⟶ Sb

DISSOLUTION OF ADHESIVE

NASAL CAVITY INSERTION DEVICE

CROSS-REFERENCE TO RELATED APPLICATIONS

This U.S. National Stage Application claims priority under 35 U.S.C. §119(a) to Japanese Patent Application No. 2010-049338, filed in Japan on Mar. 5, 2010, and Japanese Patent Application No. 2010-197663, filed in Japan on Sep. 3, 2010. The entire disclosures of Japanese Patent Application Nos. 2010-049338 and 2010-197663 are hereby incorporated herein by reference.

TECHNICAL FIELD

The present invention relates to a nasal cavity insertion device that is effective for treatment, prevention and resolution of snoring or obstructive sleep apnea syndrome (OSAS).

BACKGROUND ART

Patients of OSAS intermittently repeat a temporally suffocated state (apnea, infrequent breathing) while the pharynx of the upper respiratory tract is obstructed due to a complication of muscle relaxation and obesity and the like during sleep. Therefore, patients of OSAS are suffered from hypertension or disorders in brain blood vessels and cardiac blood vessels. Further, patients of OSAS cannot sleep sufficiently, and therefore, tend to feel drowsy in the daytime and/or tend to lack of concentration or vitality in the daytime. Yet further, when driving a car, patients of OSAS have high chances of causing an accident, a serious accident or the like due to falling asleep at the wheel.

On the other hand, similarly to OSAS, snoring occurs when the respiratory tract's mucus membranes of the pharynx and the like vibrate due to stenosis or obstruction of the upper respiratory tract during sleep. Snoring disturbs not only the sleep of a roommate but also the sound sleep of a snorer oneself, and the snorer tends to feel drowsy in the daytime or tends to lack of concentration or vitality in the daytime.

In view of the above, a variety of proposals have been made in recent years for treating or resolving OSAS or snoring. For example, such proposals include "a method of inserting a tube into the pharynx via a nasal passage (hereinafter referred to as "a tube inserting method" (e.g., Japan Laid-open Patent Application Publication No. JP-A-2009-072581)", "a method of expanding the pharynx by inserting a tube, to the tip of which a water swelling resin is applied, into the pharynx via a nasal passage, and subsequently, by swelling the water swelling resin using moisture in the periphery of the pharynx (hereinafter referred to as "a water swelling method", see e.g., Japan Laid-open Patent Application Publication No. JP-A-2009-072581)", "a method of expanding the pharynx by inserting a tube having an expansion portion in the tip thereof into the pharynx via a nasal passage, and subsequently, by expanding the expansion portion through a user's operation (hereinafter referred to as "an operational expanding method", see e.g., Japan Laid-open Patent Application Publications Nos. JP-A-2006-204630, JP-A-2009-034384, JP-A-2009-072581, JP-A-2009-072582, etc.)" and etc.

SUMMARY OF INVENTION

However, the aforementioned methods are not preferable in that: the tube inserting method has difficulty in sufficiently expanding the pharynx; the water swelling method requires too much time to completely swell the water swelling resin; and the operational expanding method forces a user to take time and effort of an operation.

It is an object of the present invention to provide a nasal cavity insertion device whereby the pharynx can be sufficiently expanded, it takes less time to set the device, and further, a user is not forced to take time and effort of an operation.

A nasal cavity insertion device according to a first aspect of the present invention includes an elastically deforming part and a water soluble holding part. The elastically deforming part is elastically deformable. It should be noted that the number of the elastically deforming part may be single or plural. Further, the elastically deforming part may be entirely formed by an elastic body, or alternatively, may be partially formed by an elastic body. The water soluble holding part holds the elastically deforming part in a diameter reduced state.

Incidentally, when the elastically deforming part enclosed with the water soluble holding part reaches the pharynx, the water soluble holding part is removed by the moisture in the surrounding of the pharynx in a short period of time. Accordingly, the elastically deforming part, held in the compressed state, is roughly restored to its original shape, and the pharynx is further expanded. Therefore, according to the nasal cavity insertion device, the pharynx can be sufficiently expanded, it takes less time to set the device, and further, a user is not forced to take time and effort of an operation.

A nasal cavity insertion device according to a second aspect of the present invention relates to the nasal cavity insertion device according to the first aspect, and wherein the elastically deforming part has at least one of the shapes of a columnar shape, a cylindrical shape, a plate shape, a multi-lumen shape and a coil spring shape. It should be noted that when multiple elastic deforming parts are provided, all the elastically deforming parts may have the same shape or may have a combination of different shapes.

Therefore, the present nasal cavity insertion device is superior in its extensibility.

A nasal cavity insertion device according to a third aspect of the present invention relates to the nasal cavity insertion device according to the first aspect of the second aspect. The present nasal cavity insertion device further includes a main body holding said at least an elastically deforming part. Further, the water soluble holding part holds at least the elastically deforming part, in a diameter reduced state, of the main body part and the elastically deforming part. It should be noted that the shape, size and material of the main body part, the position of the main body with respect to the elastically deforming part, and etc. are not particularly limited. For example, the main body part may be a tubular elastic body, a wire made of metal, or a flat-plate shaped elastic body.

Therefore, the present nasal cavity insertion device can reliably hold at least an elastically deforming part. Accordingly, when inserted into a nasal cavity, the elastically deforming part can be stably inserted into the pharynx.

A nasal cavity insertion device according to a fourth aspect of the present invention relates to the nasal cavity insertion device according to the third aspect, and wherein the elastically deforming part has an elastic plate-shaped portion being to extend to a side away from the main body part. It should be noted that the elastic plate-shape portion may be formed in a flat plate shape or a curved surface shape.

Therefore, the present nasal cavity insertion device is superior in its extensibility.

A nasal cavity insertion device according to a fifth aspect of the present invention relates to the nasal cavity insertion device according to the third aspect, and wherein the elastically deforming part is a cut-out tubular body that is cut out only at a portion thereof across an entire length thereof. It should be noted that, the outer peripheral shape of the cut-out tubular body, obtained when the cut-out tubular body is cut along a plane arranged perpendicularly to the longitudinal direction, is not particularly limited but is preferably formed in a circular shape.

Therefore, the elastically deforming member can be easily fabricated in the present nasal cavity insertion device.

A nasal cavity insertion device according to a sixth aspect of the present invention relates to the nasal cavity insertion device according to the fifth aspect, and wherein the elastically deforming part is attached to an outer peripheral surface of the main body part at a vicinity portion to the cut-out portion. Further, the water soluble holding part holds the cut-out tubular body while an inner peripheral surface of the cut-out tubular body makes contact with the main body part.

Therefore, the elastically deforming part can be roughly restored to its original shape while lifting up the pharynx even when the elastically deforming part is surrounded by the pharynx in the vicinity of the pharynx in the insertion of the nasal cavity insertion device. Therefore, the present nasal cavity insertion device is superior in its extensibility.

It should be noted that, contrarily, when the water soluble holding part holds the cut-out tubular body while the outer peripheral surface of the cut-out tubular body makes contact with the main body part, the elastically deforming part becomes easily hooked on the pharynx and it becomes difficult to sufficiently expand the pharynx.

A nasal cavity insertion device according to a seventh aspect of the present invention relates to the nasal cavity insertion device according to the fifth aspect or the sixth aspect, and wherein the elastically deforming part has a base end side portion slanted closer to the main body part towards a base end.

Therefore, the nasal cavity insertion device becomes easily pulled out of the pharynx even after the elastically deforming part is expanded.

A nasal cavity insertion device according to an eighth aspect of the present invention relates to the nasal cavity insertion device according to any one of the third to seventh aspects, and wherein a plurality of the elastically deforming parts are intermittently disposed on an outer peripheral surface of the main body part along a circumferential direction of the main body part. It should be noted that the intervals among the elastically deforming parts disposed on the outer peripheral surface of the main body part are preferably equal or symmetrical.

Therefore, the main body part can be stably held while being separated away from the wall surface of the pharynx. Accordingly, a ventilation channel related to the main body part can be stably and reliably produced, and thereby, nasal mucus can be inhibited from getting stuck within the nasal cavity insertion device.

A nasal cavity insertion device according to a ninth aspect of the present invention relates to the nasal cavity insertion device according to any of the third to eighth aspects, and wherein the main body has a hardness greater than that of the elastically deforming part.

Therefore, the main body part can be prevented from being collapsed in swallowing. Further, an uncomfortable feeling, aroused in the insertion of the nasal cavity insertion device, can be relieved by setting the hardness of the elastically deforming part to be low.

A nasal cavity insertion device according to a tenth aspect of the present invention relates to the nasal cavity insertion device according to any of the first to ninth aspects, and wherein the water soluble holding part is either a water soluble thin film that is made of wafer, gelatin or polysaccharide, or a tubular water soluble organizer that is made of wafer, gelatin or polysaccharide.

Therefore, the water soluble holding part is removed without being remained by the moisture in the periphery of the pharynx in a short period of time.

A nasal cavity insertion device according to an eleventh aspect of the present invention relates to the nasal cavity insertion device according to any of the first to tenth aspects, and wherein a portion, covering a tip of the elastically deforming part, of the water soluble holding part is formed in a dome shape with a convex on a tip side thereof.

Therefore, the elastically deforming part can smoothly reach the pharynx without hurting the mucus membrane of the inner surface of the nasal cavity. Accordingly, an uncomfortable feeling, aroused in inserting the nasal cavity insertion device into the nasal cavity, can be relieved.

A nasal cavity insertion device according to a twelfth aspect of the present invention relates to the nasal cavity insertion device according to any of the first to eleventh aspects, and wherein a contrast agent is added thereto. It should be noted that the contrast agent is, for instance, barium sulfate. Further, the position of adding the contrast agent is not particularly limited. However, the contrast agent is preferably added to the tip of the main body part and that of the elastic deforming part in order to confirm the position at the time of insertion.

Therefore, it is possible to determine whether or not the nasal cavity insertion device is disposed in a predetermined position in the pharynx.

A nasal cavity insertion device according to a thirteenth aspect of the present invention relates to the nasal cavity insertion device according to any of the first to twelfth aspects, and wherein a cross-sectional area in a portion on which the elastically deforming part is disposed is set to be greater than or equal to 15 $mm^2$ and less than or equal to 40 $mm^2$.

A required air flow amount can be reliably obtained by setting the cross-sectional area to be greater than or equal to 15 $mm^2$, while an uncomfortable feeling, aroused at the time of insertion, can be relieved by setting the cross-sectional area to be less than or equal to 40 $mm^2$. In other words, it is possible to reliably obtain an air flow channel and simultaneously to relieve an uncomfortable feeling at the time of insertion by setting the cross-sectional area to be greater than or equal to 15 $mm^2$ and less than or equal to 40 $mm^2$.

A nasal cavity insertion device according to a fourteenth aspect of the present invention relates to the nasal cavity insertion device according to any of the first to thirteenth aspects, and wherein the elastically deforming part has a longitudinal length set to be greater than or equal to 25 mm and less than or equal to 45 mm.

In this case, the flow channel of the main body part can be prevented from being obstructed by the elastically deforming part elongated in the longitudinal direction even when negative pressure is produced in the pharynx.

DESCRIPTION OF EMBODIMENTS

First Embodiment

Figure 1:
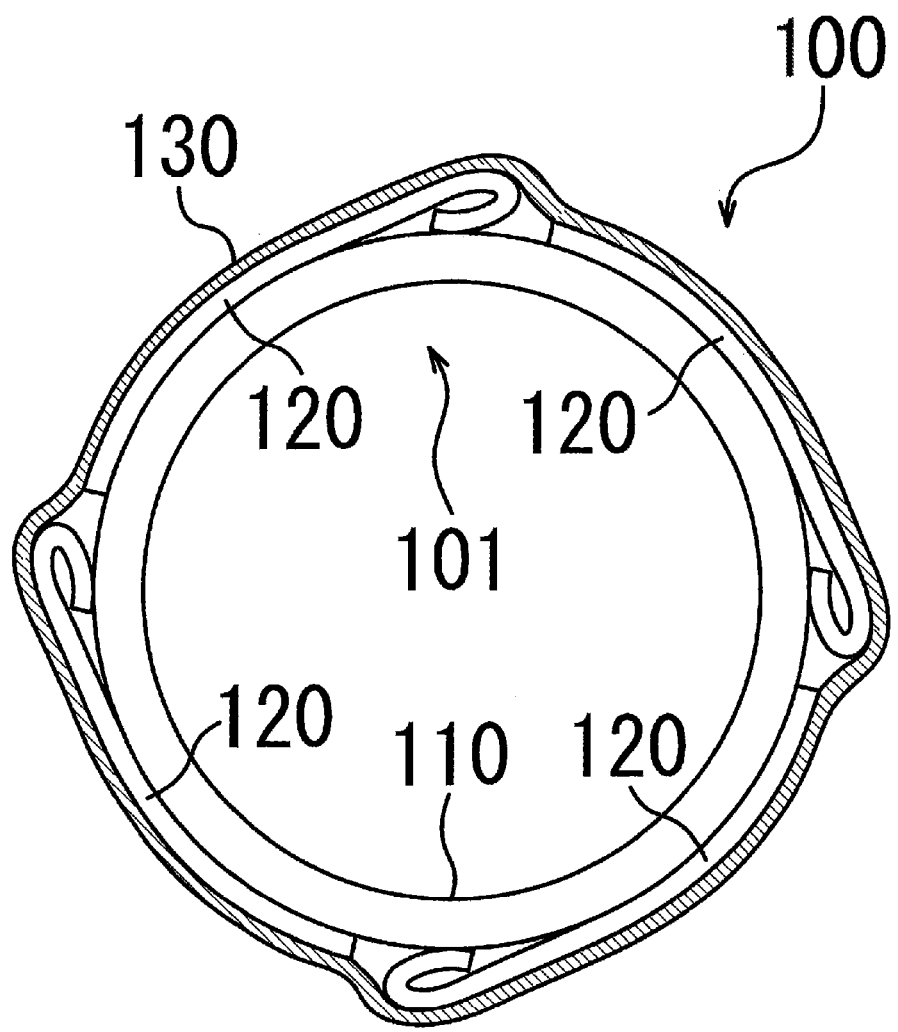
FIG. 1 is a front view of a nasal cavity insertion device according to a first embodiment of the present invention.
Figure 2:
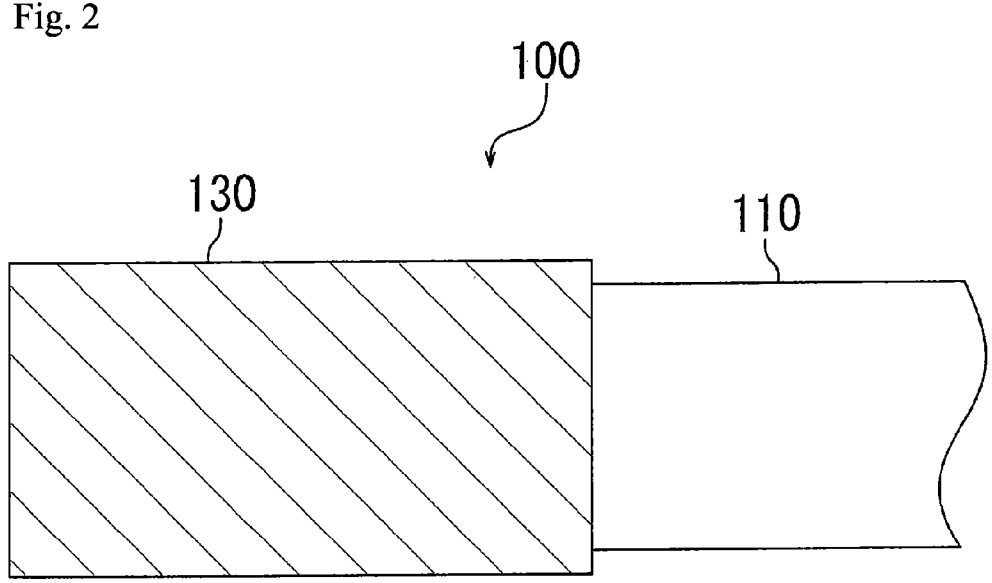
FIG. 2 is a side view of the nasal cavity insertion device according to the first embodiment of the present invention.

As shown in FIGS. 1 and 2, a nasal cavity insertion device 100 according to a first embodiment of the present invention mainly includes a main body 101 and a water film 130.

Figure 3:
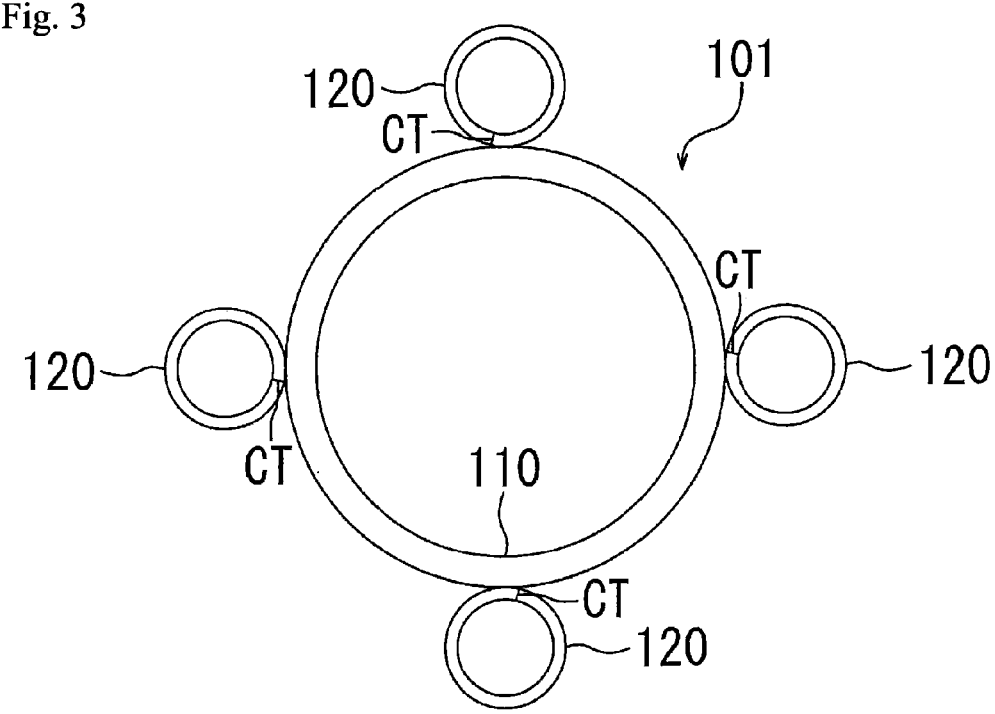
FIG. 3 is a front view of a main body of the nasal cavity insertion device according to the first embodiment of the present invention.
Figure 4:
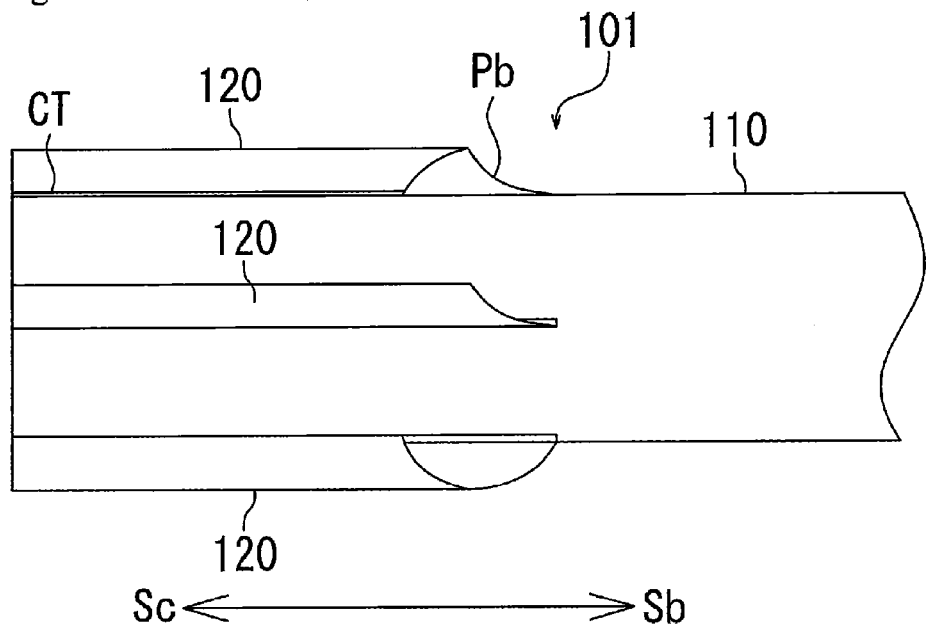
FIG. 4 is a side view of the main body of the nasal cavity insertion device according to the first embodiment of the present invention.

It should be noted that the main body 101 is restored to a shape shown in FIGS. 3 and 4 when the wafer film 130 is removed from the nasal cavity insertion device 100.

The main body 101 and the wafer film 130 will be hereinafter described in detail, respectively.

<Details of Elements of Nasal Cavity Insertion Device>

(1) Main Body

As shown in FIGS. 1 to 4, the main body 101 mainly includes a main body part 110 and elastically deforming parts 120. The main body part 110 is a tube made of silicone rubber and has a length roughly equal to the distance from the entrance of a nasal passage to the pharynx. It should be noted that a stopper (not shown in the figures) is disposed on the base end side of the main body part 110.

As shown in FIGS. 3 and 4, each elastically deforming part 120 is a tube made of silicone rubber and has a diameter less than that of the main body part 110. Each elastically deforming part 120 is cut out only at a portion thereof across the entire length thereof, and is attached to the outer peripheral surface of the main body part 110 at a vicinity portion to the cut-out portion CT. It should be noted in the present embodiment that four elastically deforming parts 120 are equally attached to the outer peripheral surface of the main body part 110. Further, in each elastically deforming part 120, a base end side portion Pb is slanted closer to the main body part in a direction from a tip end side Sc to a base end side Sb.

Further, as shown in FIGS. 1 and 2, the elastically deforming parts 120 are enclosed with the wafer film 130 while being elastically deformed so that the inner peripheral surfaces thereof make contact with the main body part 110.

(2) Wafer Film

The wafer film 130 is a translucent thin film made of starch. It should be noted that the film thickness thereof is produced by adding a predetermined thickness to the thickness enough to resist against the shape restoring force of the elastically deforming parts 120. Further, the wafer film 130 holds the four elastically deforming parts 120 while each elastically deforming part 120 is reduced in its diameter.

<Method of Using Nasal Cavity Insertion Device>

The nasal cavity insertion device 100 is inserted from the tip end side Sc into a nasal passage until the stopper makes contact with the nose. In the meantime, the wafer film 130 dissolves in the moisture in the vicinity of the pharynx and each elastically deforming part 120 is restored to the shape shown in FIGS. 3 and 4. The pharynx is thereby expanded. It should be noted that when being removed, the nasal cavity insertion device 100 may be pulled out as it is.

As described above, the nasal cavity insertion device 100 of the present embodiment includes the tubular main body part 110, the elastically deforming parts 120 attached to the outer peripheral surface of the main body part 110, and the wafer film 130 functioning as a water soluble holding part for holding the elastically deforming parts 120 in a compressed state. In other words, the nasal cavity insertion device 100 including the wafer firm 130 is in the aspect of a state before insertion into a nasal cavity. In other words, the nasal cavity insertion device 100 of a usage state includes the tubular main body part 110 and the elastically deforming parts 120 attached to the outer peripheral surface of the main body part 110.

<Features of Nasal Cavity Insertion Device>

(1) Comparison was made between a condition where the main body 101 of the nasal cavity insertion device 100 according to the first embodiment of the present invention and a condition where only the main body part 110 is used, regarding 3% oxygen desaturation frequency per unit time (i.e., frequency that degree of oxygen saturation is reduced at a reduction rate of greater than or equal to 3% per unit time) and 4% oxygen desaturation frequency (i.e., frequency that degree of oxygen saturation is reduced at a reduction rate of greater than or equal to 4% per unit time). The condition where the main body 101 is used showed a lower value than the condition where only the main body part 110 is used. This proved that the main body 101 was more advantageous than the main body part 110 alone. Therefore, the nasal cavity insertion device 100 according to the present embodiment can sufficiently expand the pharynx compared to the well-known configuration using a tube alone.

(2) In the nasal cavity insertion device 100 according to the first embodiment of the present invention, the elastically deforming parts 120 are enclosed with the wafer film 130 while being elastically deformed so that the inner peripheral surfaces thereof make contact with the main body part 110. Therefore, in the nasal cavity insertion device 100, when the wafer film 130 dissolves in the moisture in the vicinity of the pharynx, each elastically deforming part 120 is immediately restored to the original shape thereof. Therefore, it takes less time to set this nasal cavity insertion device 100.

(3) The nasal cavity insertion device 100 according to the first embodiment of the present invention does not require a user's operation for restoring each elastically deforming part to the original shape thereof. Therefore, the nasal cavity insertion device 100 does not force a user to take time and effort of an operation.

Second Embodiment

Figure 9:
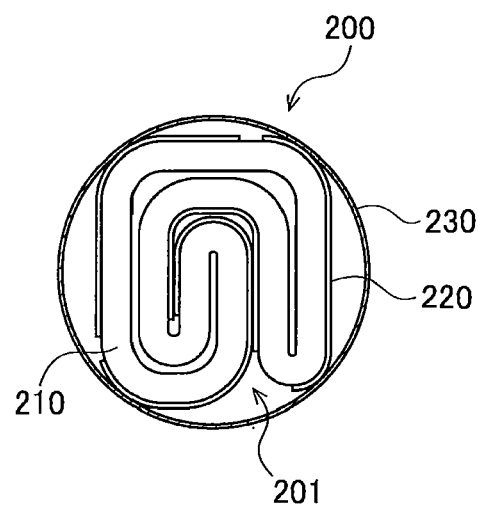
FIG. 9 is a front view of a nasal cavity insertion device according to a second embodiment of the present invention.

As shown in FIG. 9, a nasal cavity insertion device 200 according to a second embodiment of the present invention mainly includes a main body 201 and a gelatin organizer 230.

Figure 10:
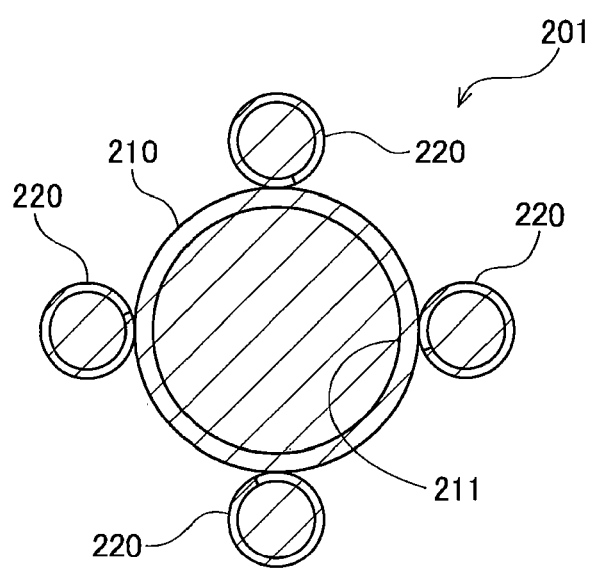
FIG. 10 is a front view of a main body of the nasal cavity insertion device according to the second embodiment of the present invention.

It should be noted in the second embodiment that the main body 201 is restored to a shape shown in FIG. 10 when the gelatin organizer 230 is removed from the nasal cavity insertion device 200.

The main body 201 and the gelatin organizer 230 will be hereinafter described in detail, respectively.

<Details of Elements of Nasal Cavity Insertion Device>

(1) Main Body

As shown in FIG. 10, the main body 201 mainly includes a main body part 210 and elastically deforming parts 220.

Figure 11:
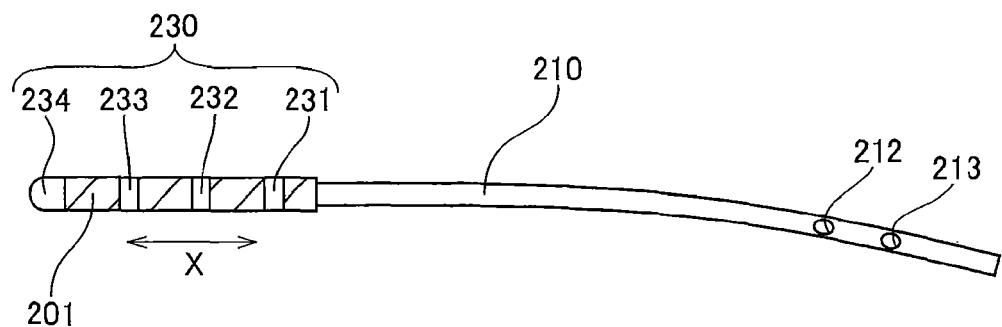
FIG. 11 is a side view of the nasal cavity insertion device according to the second embodiment of the present invention.

The main body part 210 is a tube made of silicone rubber and has a length roughly equal to the distance from the entrance of a nasal passage to the pharynx. It should be noted that a stopper (not shown in the figures) is disposed on the base end side of the main body part 210. Further, as shown in FIG. 11, the main body part 210 has two openings 212 and 213 on the base end side portion thereof, and the openings 212 and 213 are communicated with a ventilation channel 211 (see FIG. 10) produced in the inside of the main body part 210. Thus, the openings 212 and 213 are formed in the portion closer to a nasal passage in the attachment of the nasal cavity insertion device 200. This allows a patient to easily breathe. Further in the present embodiment, as shown in FIG. 11, the main body part 210 is formed in a bent shape for relieving the uncomfortable feeling aroused in the insertion of the nasal cavity insertion device 200.

Further, the hardness of the main body part 210 is set to be higher than that of each elastically deforming part 220. Specifically, the hardness of the main body part 210 is A70, whereas the hardness of each elastically deforming part 220 is A60. It should be noted that the hardness herein described is based on the type A durometer hardness prescribed in JIS K6253.

As shown in FIG. 10, similarly to the elastically deforming parts 120 of the first embodiment, each elastically deforming part 220 is a tube made of silicone rubber and has a diameter (e.g., 1.8 mm) less than that of the main body part 210 (e.g., 4.0 mm). Four elastically deforming parts 220 are herein disposed on the outer peripheral surface of the main body part 210 while being intermittently aligned along the circumferential direction of the main body part 210. In other words, the four elastically deforming parts 220 are disposed on the outer peripheral surface of the main body part 210 while being equally aligned at 90-degree intervals along the circumferential direction of the main body part 210.

Figure 12:
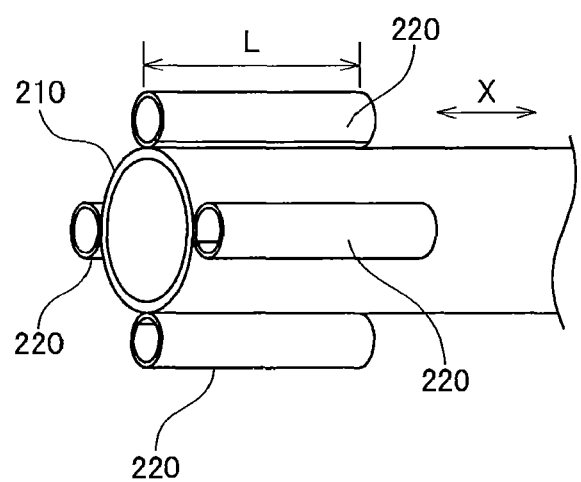
FIG. 12 is a perspective view of the main body of the nasal cavity insertion device according to the second embodiment of the present invention.

Further, as shown in FIG. 12, each elastically deforming part 220 has a longitudinal (X-directional) length L set to be greater than or equal to 25 mm and less than or equal to 45 mm.

Further, in a part on which the elastically deforming parts 220 are disposed, a cross section (a hatched region in FIG. 10), which is cut along a plane arranged perpendicularly to the longitudinal direction (X direction) of the elastically deforming parts 220, is set to have an area that is greater than or equal to 15 mm$^2$ and less than or equal to 40 mm$^2$.

Further, a contrast agent (e.g., barium sulfate, etc.) is added to at least either of the aforementioned main body part 210 and the aforementioned elastically deforming parts 220. It should be noted that the contrast agent is at least added to the tip portion of the nasal cavity insertion device 200.

(2) Gelatin Organizer

As shown in FIG. 9, the main body part 210 and the elastically deforming parts 220 are held by the gelatin organizer 230 while being compressed and deformed. As shown in FIG. 11, the gelatin organizer 230 is formed by three cylindrical holders 231 to 233 and a holder 234 having a dome-shaped tip portion. The gelatin organizer 230 is a translucent member made of gelatin.

It should be noted that the nasal cavity insertion device 200 includes the tubular main body part 210, the elastically deforming parts 220 attached to the outer peripheral surface of the main body part 210, and the gelatin organizer 230 functioning as a water soluble holding part for holding the elastically deforming parts 220 in a compressed state. In other words, the nasal cavity insertion device 200 including the gelatin organizer 230 is in the aspect of the state before insertion into a nasal cavity. In other words, the nasal cavity insertion device 200 of the usage state includes the tubular main body part 210 and the elastically deforming parts 220 attached to the outer peripheral surface of the main body part 210.

<Method of Using Nasal Cavity Insertion Device>

The nasal cavity insertion device 200 is inserted from the tip side thereof into a nasal passage until the stopper makes contact with the nose. In the meantime, the gelatin organizer 230 dissolves in the moisture in the vicinity of the pharynx and each elastically deforming part 220 is restored to the shape shown in FIG. 10. The pharynx is thereby expanded. It should be noted that when being removed, the nasal cavity insertion device 200 may be pulled out as it is.

<Method of Folding Main Body>

Figure 13:
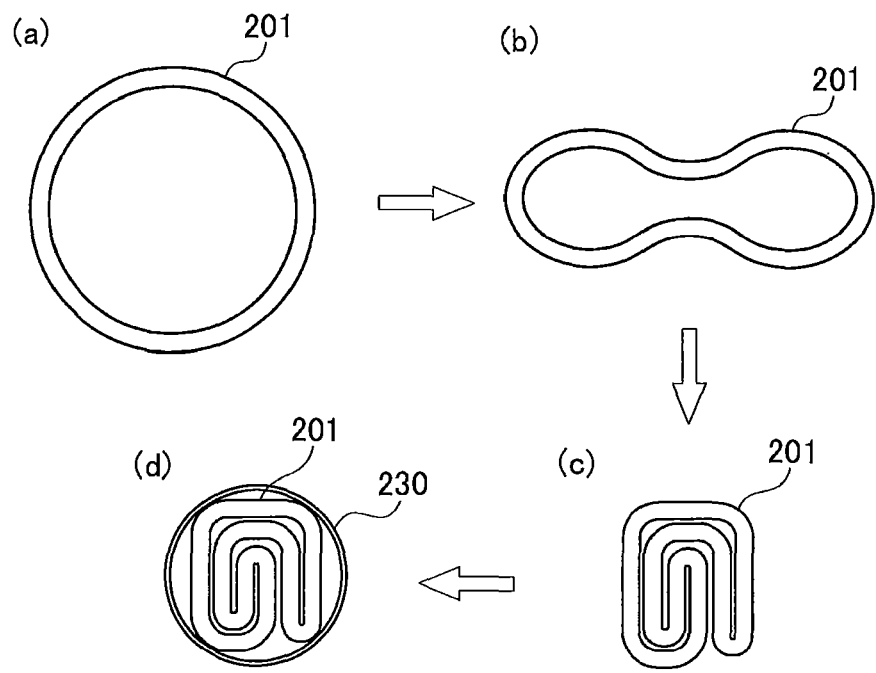
FIG. 13 is a schematic diagram for explaining a method of folding the main body of the nasal cavity insertion device according to the second embodiment of the present invention.
Figure 14:
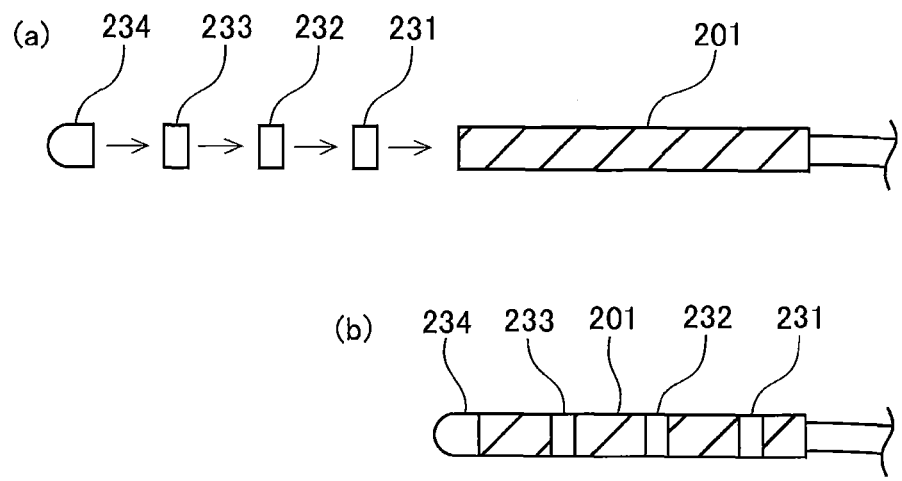
FIG. 14 is a schematic diagram for explaining a method of attaching a gelatin organizer to the main body of the nasal cavity insertion device according to the second embodiment of the present invention.

Next, a method of folding the main body 201 (the main body part 210 and the elastically deforming parts 220) will be explained with reference to FIGS. 13 and 14. It should be noted in FIG. 13 that only the main body part 210 is illustrated without illustrating the elastically deforming parts 220 for the sake of simple illustration of the figures. First, the main body 201 is prepared as shown in FIG. 13(*a*). As shown in FIG. 13(*b*), the main body 201 is compressed from the top and bottom sides thereof and from the right and left sides thereof, and is thereby formed in a roughly flattened shape. Then, the flattened main body 201 is wound in a roll shape as shown in FIG. 13(*c*). Subsequently, the gelatin organizer 230 (the holders 231 to 234) is attached to the roll-shaped main body 201 as shown in FIGS. 13(*d*), 14(*a*) and 14(*b*). Accordingly, the outermost diameter of the nasal cavity insertion device 200 is set to be less than or equal to 5.0 mm.

<Features of Nasal Cavity Insertion Device>

(1) The nasal cavity insertion device 200 according to this second embodiment has a feature similar to the aforementioned feature (1) of the nasal passage insertion device 100 according to the first embodiment and achieves advantageous effects similar to those achieved by the nasal passage insertion device 100.

(2) Further, in the nasal cavity insertion device 200 according to the second embodiment of the present invention, the main body part 210 and the elastically deforming parts 220 are held by the gelatin organizer 230 while being compressed and deformed. Therefore, in the nasal cavity insertion device 200, when the gelatin organizer 230 dissolves in the moisture in the vicinity of the pharynx, the main body part 210 and the elastically deforming parts 220 are immediately restored to the original shapes thereof. Therefore, it takes less time to set the nasal cavity insertion device 200.

(3) Further, the nasal cavity insertion device 200 according to the second embodiment of the present invention does not require a user's operation for restoring the elastically deforming parts 220 to the original shapes thereof. Therefore, the nasal cavity insertion device 200 does not force a user to take time and effort of an operation.

(4) Further, in the nasal passage insertion device 200 according to the second embodiment of the present invention, the tubular water soluble organizer made of gelatin (the gelatin organizer 230) is used. Therefore, the gelatin organizer 230 can be removed in a short time without being remained. Accordingly, the elastically deforming parts 220 are appropriately restored and expanded to the original states thereof. The pharynx can be thereby expanded.

(5) Further, in the nasal cavity insertion device 200 according to the second embodiment of the present invention, the tips of the elastically deforming parts 220 are covered with the dome-shaped gelatin organizer 230 (the holder 234). Therefore, the elastically deforming parts 220 can smoothly reach the pharynx without damaging the inner surface mucus membrane of a nasal cavity. Accordingly, uncomfortable feeling can be relieved in inserting the nasal cavity insertion device 200 into a nasal cavity.

Figure 15:
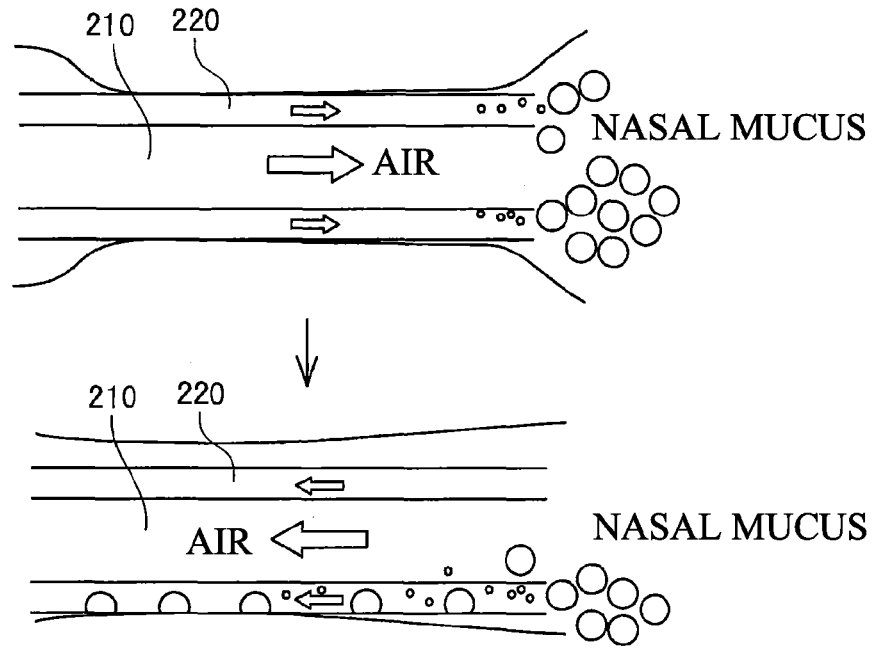
FIG. 15 is a schematic diagram for explaining an effect of the nasal cavity insertion device according to the second embodiment of the present invention.

(6) Further, as shown in FIG. 15, the elastically deforming parts 220 of the nasal cavity insertion device 200 according to the second embodiment of the present invention works for separating the main body part 210 away from the inner peripheral surface of the pharynx. Therefore, a ventilation channel can be reliably produced in a position where the ventilation cannel does not make contact with the inner peripheral surface of the pharynx. Accordingly, the ventilation channel related to the main body part 210 can be reliably produced even when breathability is lost due to the nasal mucus in the vicinity of the inner peripheral surface of the pharynx. Nasal mucus can be thereby suppressed from getting stuck in the nasal passage insertion device 200.

In a model experience conducted using egg albumen for proving the aforementioned effect, it was confirmed that egg albumen got stuck less in the use of the main body 201 including the elastically deforming parts 220 than in the use of a simple cylindrical main body part including no elastically deforming part.

(7) Further, the nasal cavity insertion device 200 according to the second embodiment of the present invention includes the four elastically deforming parts 220 that are intermittently disposed along the circumferential direction of the main body part 210. Therefore, the main body part 210 can be stably held while being separated away from the inner peripheral surface of the pharynx. Accordingly, a ventilation channel related to the main body part 210 can be stably and reliably produced. This can reliably suppress nasal mucus from getting stuck within the nasal cavity insertion device 200.

(8) Further, the contrast agent is added to at least either of the main body part 210 and the elastically deforming parts 210 of the nasal cavity insertion device 200 according to the second embodiment of the present invention. Therefore, it is possible to determine whether or not the nasal cavity insertion device 200 is disposed in a predetermined position in the pharynx.

(9) Further, a model experiment was conducted for a flow rate using the nasal cavity insertion device 200 according to the second embodiment of the present invention. In the experiment, it was proved that air can flow without resistance at an appropriate flow rate within the nasal cavity insertion device 200 when a cross section, cut along a plane arranged perpendicularly to the longitudinal direction (X direction) of the elastically deforming parts 220, is set to have an area greater than or equal to 15 mm$^2$ in a part on which the elastically deforming parts 220 are disposed. Further, it was also proved that a remarkable effect cannot be expected so much even if the cross-sectional area is set to be too large. On the other hand, when the cross-sectional area is set to be less than or equal to 40 mm$^2$, uncomfortable feeling can be relieved in the insertion of the nasal cavity insertion device 200.

(10) Further, a model experiment was conducted for a flow rate using the nasal cavity insertion device 200 according to the second embodiment of the present invention. In the experiment, it was proved that even if a negative pressure is produced in the pharynx, the elastically deforming parts 220 are prevented from obstructing the flow channel of the main body part 210 when the longitudinal length of each elastically deforming part 220 is set to be greater than or equal to 25 mm and less than or equal to 45 mm.

(11) Further, in the nasal cavity insertion device 200 according to the second embodiment of the present invention, the main body part 210 can be prevented from being collapsed in swallowing by setting the hardness of the main body part 210 to be greater than that of each elastically deforming part 220. Further, uncomfortable feeling can be relieved in the insertion of the nasal cavity insertion device 200 by setting the hardness of each elastically deforming part 220 to be less than that of the main body part 210. It should be noted that it is effective to increase the film thickness of the main body part 210 from the perspective of preventing the main body part 210 from being collapsed in swallowing. In the second embodiment, the film thickness of the main body part 210 is set to be 700 μm.

<Modifications>

Figure 5:
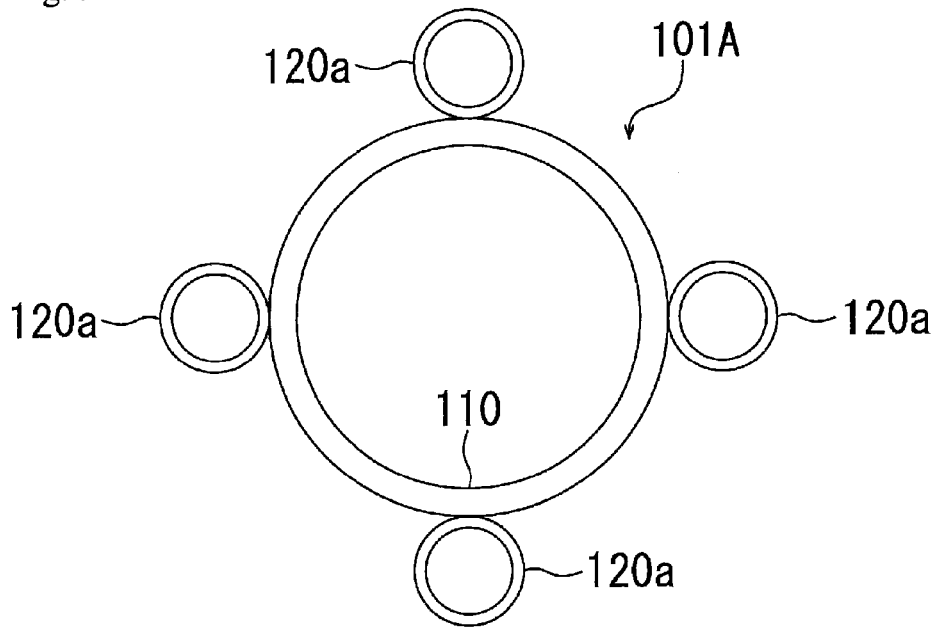
FIG. 5 is a front view of a main body of a nasal cavity insertion device according to a modification (A).

(A) In the nasal cavity insertion device 100, 200 according to the aforementioned embodiments, each elastically deforming part 120, 220 is a tube cut out only at a portion thereof across the entire length thereof. However, each elastically deforming part may be a normal tube 120a that is not cut out as shown in FIG. 5. In this case, the elastically deforming parts are enclosed with the wafer film 130 while the tubes 120a are pressed onto the main body part 110. It should be noted that a reference numeral 101A in FIG. 5 indicates "a main body" according to the present modification.

Figure 6:
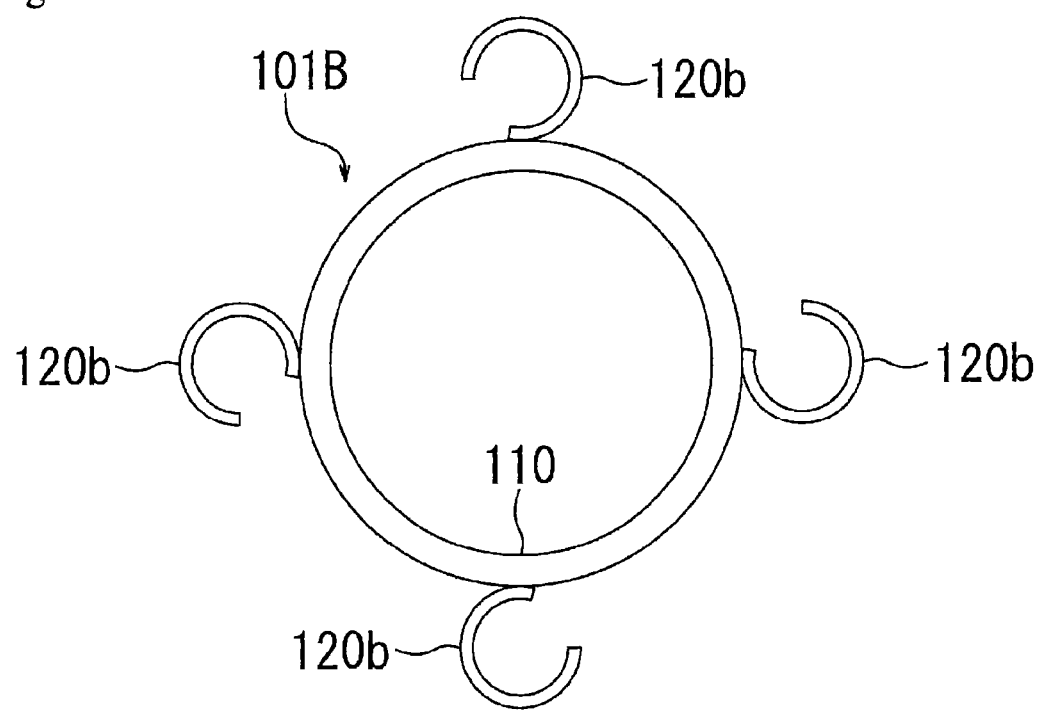
FIG. 6 is a front view of a main body of a nasal cavity insertion device according to a modification (B).

(B) In the nasal cavity insertion device 100, 200 according to the aforementioned embodiments, each elastically deforming part 120, 220 is a tube cut out only at a line thereof across the entire length thereof. However, each elastically deforming part may be a tube 120b that is cut out only at a portion thereof across the entire length thereof as shown in FIG. 6. In this case, the elastically deforming parts are enclosed with the wafer film 130 or the gelatin organizer 230 while being elastically deformed so that the inner peripheral surfaces thereof make contact with the main body part 110, 210, similarly to the elastically deforming parts 120 and 220 according to the aforementioned embodiments. It should be noted that a reference numeral 101B in FIG. 6 indicates "a main body" according to the present modification.

Figure 7:
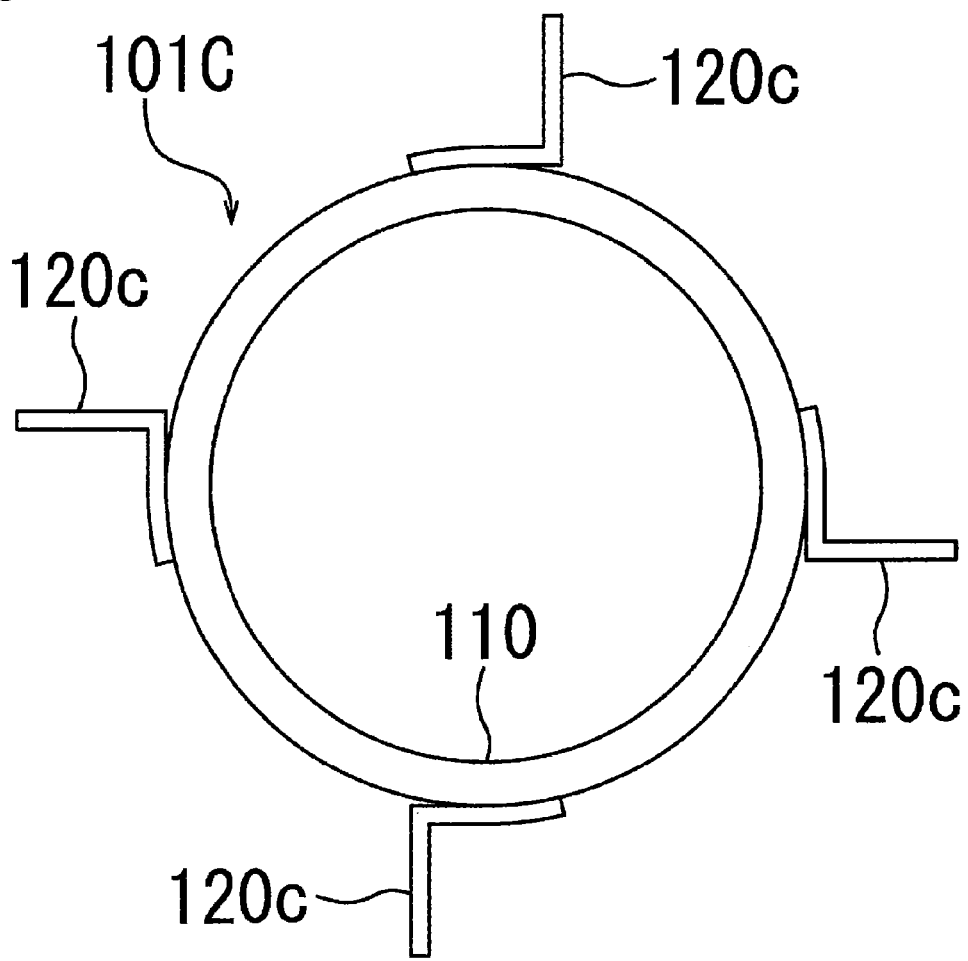
FIG. 7 is a front view of a main body of a nasal cavity insertion device according to a modification (C).

(C) In the nasal cavity insertion device 100, 200 according to the aforementioned embodiments, each elastically deforming part 120, 220 is a tube cut out only at a portion thereof across the entire length thereof. However, each elastically deforming part may be an elongated plate member 120c having an L-shaped cross-section as shown in FIG. 7. In this case, the elastically deforming parts are enclosed with the wafer film 130 or the gelatin organizer 230 while an upstanding portion of each elongated plate member 120c is pressed onto the closely contacted portion of the elongated plate member 120c. It should be noted that a reference numeral 101C in FIG. 7 indicates "a main body" according to the present modification.

Figure 8:
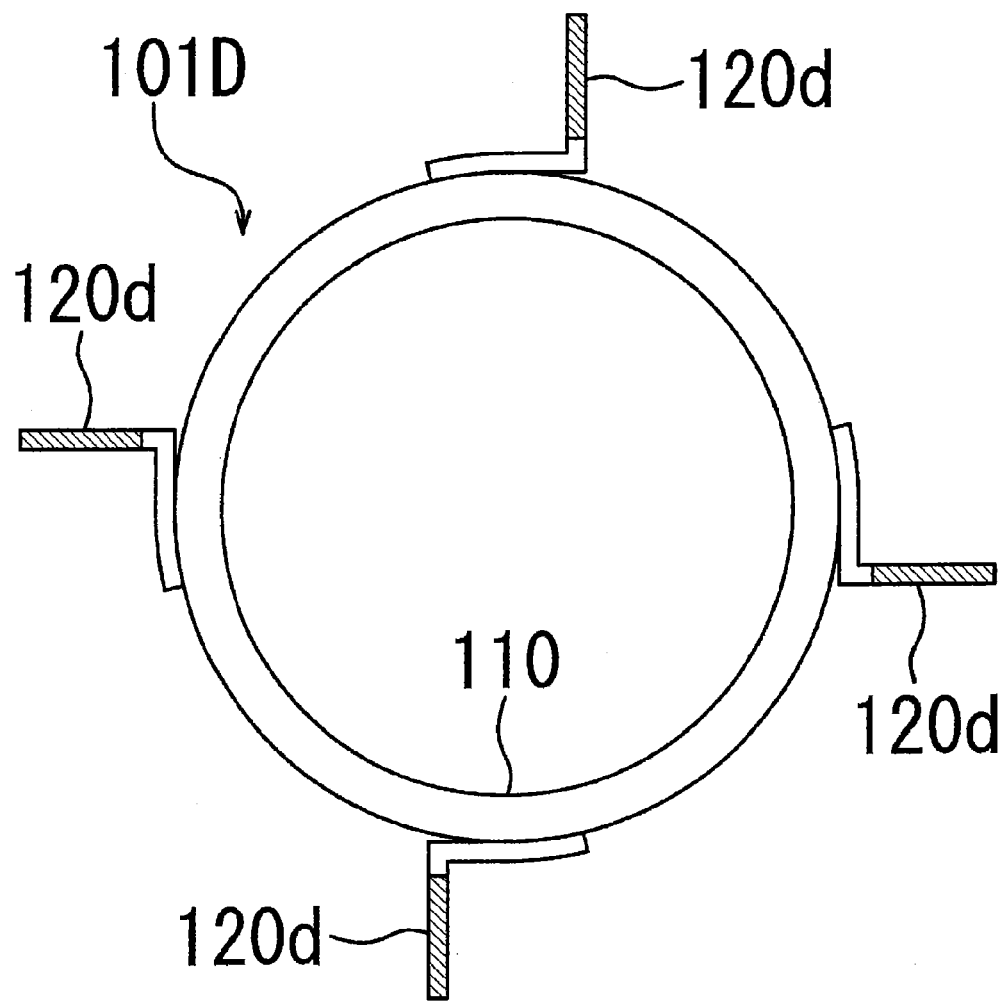
FIG. 8 is a front view of a main body of a nasal cavity insertion device according to another example of the modification (C).

Further in this case, as shown in FIG. 8, each upstanding portion 120d may be formed by a synthetic member. It should be noted that a reference numeral 101D in FIG. 8 indicates "a main body" according to another example of the present modification.

(D) The nasal cavity insertion device 100 according to the aforementioned embodiment employs the planar wafer film 130. However, the wafer film may have a strap shape. In this case, the wafer film is helically wound about the main body 101.

(E) The nasal cavity insertion device 100 according to the aforementioned embodiment employs the wafer film 130 as a water soluble holding part, whereas the nasal cavity insertion device 200 employs the gelatin organizer 230 as a water soluble holding part. However, the present invention is not limited to the above configurations, and either a water soluble thin film made of either gelatin or polysaccharide or a water soluble organizer made of either wafer or polysaccharide may be used as a water soluble holding part. Examples of the aforementioned polysaccharide include amylose, amylopectin, mannan, pullulan, guar gum, soybean polysaccharide, agar, cellulose, pectin, carrageenan, sodium alginate, arabinoxylan, and derivatives of the above.

(F) In the nasal cavity insertion device 100, 200 according to the aforementioned embodiments, the main body part 110, 210 and the elastically deforming parts 120, 220 are made of silicone rubber. However, the following materials can be applied as the material forming the main body part 110, 210 and the elastically deforming parts 120, 220. Examples are: polyurethane (urethane rubber); ethylene-propylene rubber; ethylene-propylene-diene rubber; butyl rubber; halogenated butyl rubber; ethylene-vinyl acetate copolymer; hexyne rubber; metallocene polymerized polyolefine; chlorinated polyethylene; fluorine-contained rubber; polydiene rubber; natural rubber; styrene-series thermoplastic elastomer; polyester-series thermoplastic elastomer; polyolefin-series thermoplastic elastomer; fluorinated thermoplastic elastomer; soft polyvinyl chloride; polymer alloy material containing silicone rubber as a component; polymer alloy material containing polyurethane as a component; polymer alloy material containing thermoplastic elastomer as a component; polymer alloy material containing polyvinyl chloride as a component; polymer alloy material containing hydrophilic polymer as a component; polymer alloy material containing biologically and naturally derived material as a component; polymer alloy material containing polylactic acid as a component; polypeptide; hydrogel; heparinized polymer; and phosphoserine polymer.

Further, regarding the main body parts 110 and 210, a metal, a resin and a resin coated metal can be applied in addition to the aforementioned listed materials. It should be noted that the aforementioned resin and resin coated metal include, for instance, ABS resin (acrylonitrile-butadiene-styrene), butadiene-styrene rubber, polyester copolymer, ethylene-propylene rubber (ethylene-propylene-terpolymer rubber), EVA resin (ethylene-vinylacetate copolymer), high-density polyethylene, high-density polypropylene, impact-resistant polystyrene, low-density polyethylene, methyl-methacrylate-acrylonitrile-butadiene-styrene copolymer, chloroprene rubber, nitrilebutadiene rubber, polyamide resin, PETG resin, polyacetal resin, polybutyleneterephthalate resin, polycarbonate resin, polyethersulfone resin, polyethylene resin, polyethyleneterephthalate resin, polyimide resin, isobutylene-isoprene copolymer, polypropylene resin, polystyrene resin, polysulfone resin, polytetrafluoroethylene resin, polyurethane resin, polyvinylacetate resin, polyvinylchloride resin, styrene-butadiene resin, and styrene-butadiene rubber.

Figure 16:
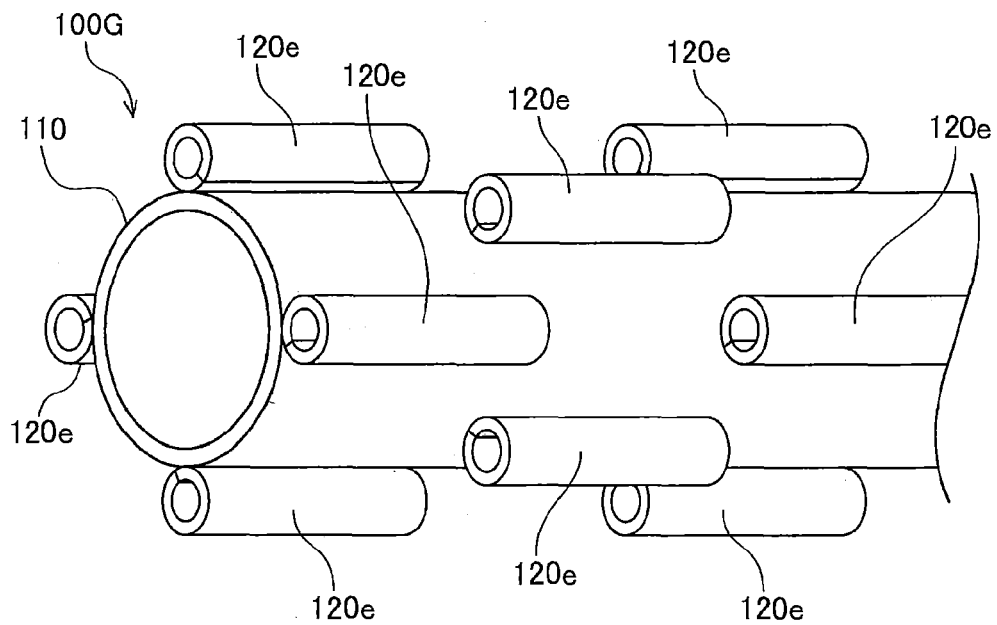
FIG. 16 is a perspective view of a main body of a nasal cavity insertion device according to a modification (G).

(G) In the nasal cavity insertion device 100, 200 according to the aforementioned embodiments, the examples have been explained that the elastically deforming parts 120, 220 are disposed at 90-degree intervals along the circumferential direction of the main body part 110, 210. However, the present invention is not limited to the configurations, and as shown in FIG. 16, elastically deforming parts 120e may be disposed in a checked shape when the main body part 110 is cut and developed in a direction arranged along the longitudinal direction (X direction).

Figure 17:
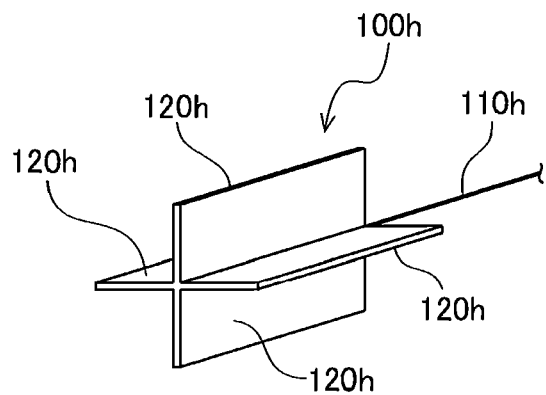
FIG. 17 is a perspective view of a nasal cavity insertion device according to a modification (H).

(H) In the nasal cavity insertion device 100, 200 according to the aforementioned embodiments, the examples have been explained that the tubular main body part 110, 210 and the tubular elastically deforming parts 120, 220 are provided. However, the present invention is not limited to the configurations, and as shown in FIG. 17, a main body part 110$h$ may be a wire rod, while elastically deforming parts 120$h$ may be respectively formed in a plate shape. In other words, a nasal cavity insertion device 100$h$ according to the present modification includes the main body part 110$h$ as a wire rod (e.g., wire) and four plate-shaped elastically deforming parts 120$h$ radially attached (at roughly 90-degree intervals) to the main body part 110$h$. It should be noted that the nasal cavity insertion device 100$h$ shown in FIG. 17 is the nasal passage insertion device 100$h$ in a state that the water soluble holding part dissolves (i.e., a usage state). Therefore, the water soluble holding part is not shown in the figure. In other words, the nasal cavity insertion device 100$h$ before insertion into a nasal cavity is obviously held while each elastically deforming part 120$h$ is reduced in its diameter by the water soluble holding part. Specifically, the four plate-shaped elastically deforming parts 120$h$ are circumferentially wound about the main body part 110$h$ as an axis and are accordingly reduced in their diameters. In modifications shown in FIGS. 18 to 31, 33 and 34, each nasal cavity insertion device is similarly in a state that the water soluble holding part dissolves. It should be noted that the number of the elastically deforming parts 120$h$ is not limited to four.

Figure 18:
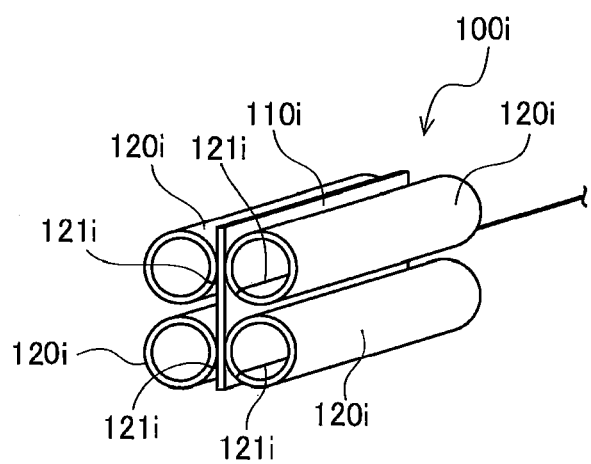
FIG. 18 is a perspective view of a nasal cavity insertion device according to a modification (I).
Figure 19:
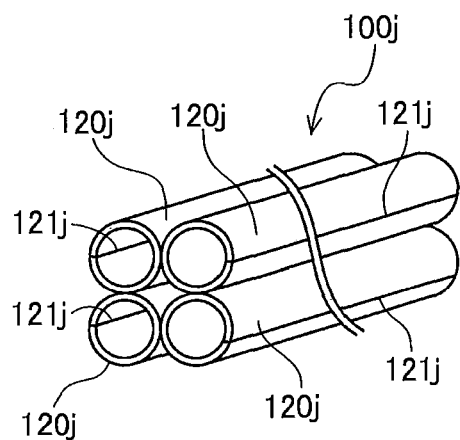
FIG. 19 is a perspective view of a nasal cavity insertion device according to a modification (J).

(I) In the nasal cavity insertion device 100, 200 according to the aforementioned embodiments, the examples have been explained that the tubular main body part 110, 210 is provided. However, the present invention is not limited to the configurations, and as shown in FIG. 18, the main body part 110$h$ may be a board as an elastic body. In other words, a nasal cavity insertion device 100$i$ according to the present modification includes a main body part 110$i$ that is a board as an elastic body, and four elastically deforming parts 120$i$ held on one surface and the other surface of the main body part 110$i$. It should be noted that the number of the elastically deforming parts 120$i$ is not limited to four. Further, the elastically deforming parts of the other modifications can be applied as the elastically deforming parts 120$i$. In the present nasal cavity insertion device 100$i$, each elastically deforming part 121$i$ can be developed in a plate shape by forming a notch 121$i$ in each elastically deforming part 120$i$. Therefore, the nasal cavity insertion device 100$i$ is reduced in its diameter by rolling up the elastically deforming parts 121$i$ developed in a plate shape together with the main body part 110$i$ and by holding the elastically deforming parts 121$i$, which are rolled up in a diameter reduced state, and the main body part 110$i$ by means of a water soluble holding part (not shown in the figure).

(J) In the nasal cavity insertion device 100, 200 according to the aforementioned embodiments, the examples have been explained that the elastically deforming parts 120, 220 are held by the main body part 110, 210. In the present invention, however, the main body part 110, 210 is not necessarily a required element. In other words, a nasal cavity insertion device 100$j$ according to the present modification shown in FIG. 19 includes four tubular elastically deforming parts 120$j$ connected to each other. The four elastically deforming parts 120$j$ are adhered to each other by means of an adhesive or the like. It should be noted that the number of the elastically deforming parts 120$j$ is not limited to four. In the present nasal cavity insertion device 100$j$, each elastically deforming part 121$i$ can be developed in a plate shape by forming a notch 121$i$ in each elastically deforming part 120$j$. Accordingly, the nasal cavity insertion device 100$i$ is reduced in its diameter by rolling up the four developed elastically deforming parts 121$i$, and further, by holding the elastically deforming parts 121$i$ rolled up in a diameter reduced state by means of a water soluble holding part (not shown in the figure).

Figure 20:
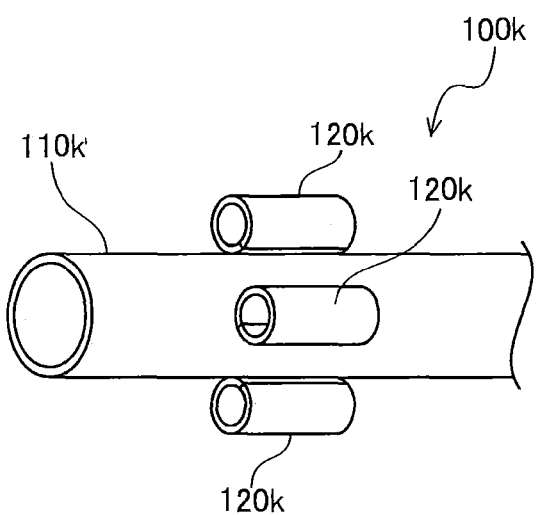
FIG. 20 is a perspective view of a nasal cavity insertion device according to a modification (K).
Figure 21:
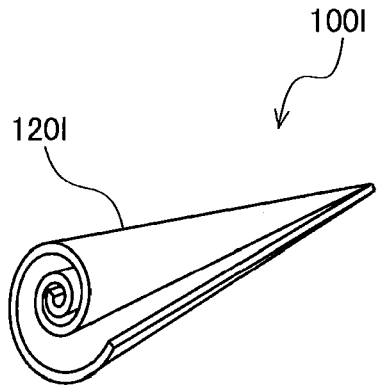
FIG. 21 is a perspective view of a nasal cavity insertion device according to a modification (L).
Figure 22:
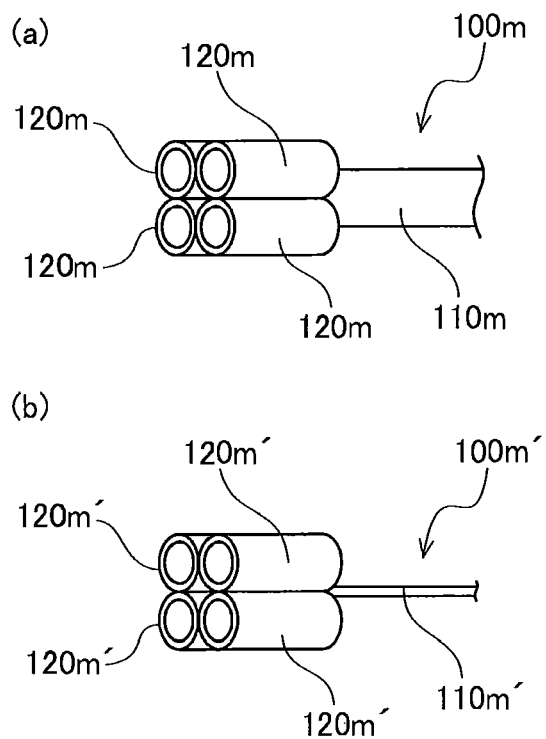
FIG. 22 is a perspective view of a nasal cavity insertion device according to a modification (M).

(K) In the nasal cavity insertion device 100, 200 according to the aforementioned embodiments, the examples have been explained that the elastically deforming parts 120, 220 are disposed on the tip of the main body part 110, 210. However, the present invention is not limited to the configurations, and as shown in FIG. 20, a plurality of elastically deforming parts 120$k$ may be disposed in positions displaced towards the base end from the tip end of a main body part 110$k$. In other words, a nasal cavity insertion device 100$k$ according to the present modification shown in FIG. 20 includes the tubular main body part 110$k$ and the multiple elastically deforming parts 120$k$ disposed on the outer peripheral surface of the main body part 110$k$ while being displaced from the tip towards the base end of the main body part 110$k$. It should be noted that similarly to the aforementioned first embodiment, the nasal cavity insertion device 100$k$ is reduced in its diameter while the elastically deforming parts 120$k$ are held by a water soluble holding part (not shown in the figure), with the inner peripheral surface of each elastically deforming part 120$k$ making contact with the outer peripheral surface of the main body part 110$k$.

(L) In the nasal cavity insertion device 100, 200 according to the aforementioned embodiments, the examples have been explained that the tubular elastically deforming parts 120, 220 are provided. However, the present invention is not limited to the configurations, and as with a nasal cavity insertion device 100$l$ according to the present modification shown in FIG. 21, a sheet-shaped elastically deforming part 120$l$ may be rolled up, and the rolled-up elastically deforming part 120$l$ may be reduced in its diameter by a water soluble holding part (not shown in the figure). The sheet-shaped elastically deforming part 120$l$ is a flexible sheet, and the tip of the elastically deforming part 120$l$ is increased in its diameter when the aforementioned water soluble holding part dissolves in the moisture in the vicinity of the pharynx. Thus, the elastically deforming part 120$l$ is changed into a roughly conical shape.

(M) In the nasal cavity insertion device 100, 200 according to the aforementioned embodiments, the examples have been explained that the elastically deforming parts 120, 220 are attached to the outer peripheral surface of the main body part 110, 210. However, the present invention is not limited to the configurations, and as with a nasal cavity insertion device 100$m$ according to the present modification shown in FIG. 22($a$), the positions, at which elastically deforming parts 120$m$ are attached to a tubular main body part 110$m$, may be on the tip side of the main body part 110$m$. Further, as with a nasal cavity insertion device 100$m$' according to the present modification shown in FIG. 22($b$), the position, at which elastically deforming parts 120$m$' are attached to a main body part 110$m$' formed by a wire, may be on the tip side of the main body part 110$m$'.

Figure 23:
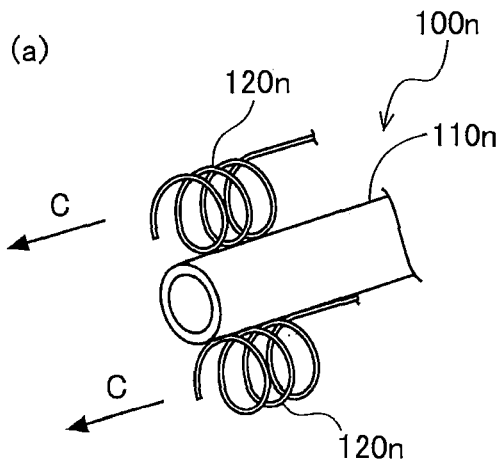
FIG. 23 is a perspective view of a nasal cavity insertion device according to a modification (N).
Figure 23:
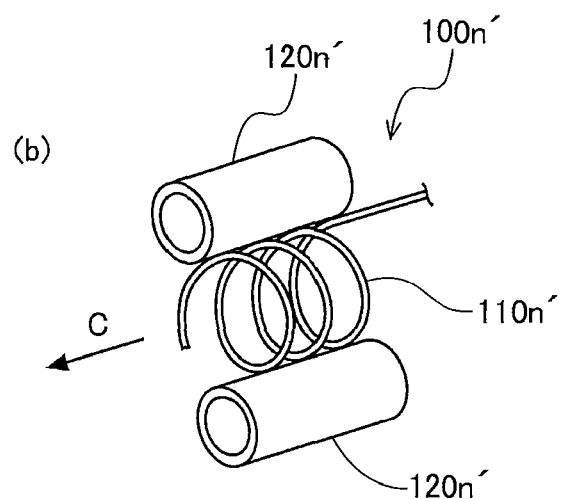
Figure 23:
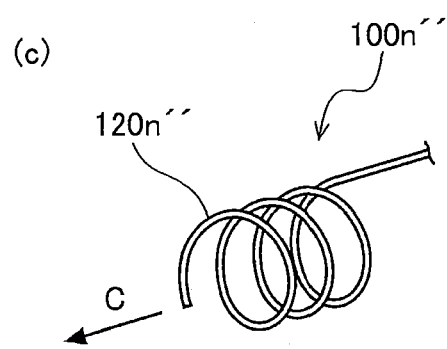

(N) In the nasal cavity insertion device 100, 200 according to the aforementioned embodiments, the examples have been explained that the elastically deforming parts 120, 220 are tubes made of silicone rubber. However, the present invention is not limited to the configurations, and as shown in FIG. 23($a$), elastically deforming parts 120$n$ may be coil springs. In other words, a nasal cavity insertion device 100$n$ according the present modification shown in FIG. 23($a$)

includes a tubular main body part 110*n* and the elastically deforming parts 120*n* formed by coil springs.

Alternatively, as shown in FIG. 23(*b*), a nasal cavity insertion device 100*n*' according to the present modification may include a main body part 110*n*' formed by a coil spring and tubular elastically deforming parts 120*n*' disposed on the outer periphery of the main body part 110*n*'.

Yet alternatively, as shown in FIG. 23(*c*), a nasal cavity insertion device 100*n*'' according to the present modification may include an elastically deforming part 120*n*'' formed by a coil spring without including a main body part as an element.

The aforementioned elastically deforming parts 120*n* and 120*n*'' and the main body part 110*n*', respectively formed by a coil spring, are pulled in the direction of the center axis of each coil spring (i.e., an arrow C direction) for reducing their diameters. The elastically deforming parts 120*n* and 120*n*'' and the main body part 110*n*', reduced in their diameters, are held by a water soluble holding part (not shown in the figures).

It should be noted that in the nasal cavity insertion device 100*n* shown in FIG. 23(*a*), each elastically deforming part 120*n* formed by a coil spring is supported at one point with respect to the main body part 110*n* for allowing each elastically deforming part 120*n* to be extended and contracted in the center axis direction (i.e., the arrow C direction). Further, similarly in the nasal cavity insertion device 100*n*' shown in FIG. 23(*b*), the main body part 110*n*' formed by a coil spring supports each elastically deforming part 120*n*' at one point so as to be extendable and contractable in the center axis direction (i.e., the arrow C direction).

Figure 24:
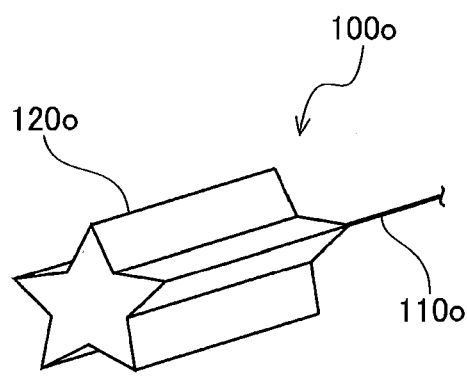
FIG. 24 is a perspective view of a nasal cavity insertion device according to a modification (O).

(O) In the nasal cavity insertion device 100, 200 according to the aforementioned embodiments, the examples have been explained that the tubular elastically deforming parts 120, 220 are provided. However, the present invention is not limited to the configurations, and as shown in FIG. 24, an elastically deforming part 120*o* may be formed in an irregular shape. In other words, a nasal cavity insertion device 100*o* according to the present modification shown in FIG. 24 includes a main body part 110*o* formed by a wire and the elastically deforming part 120*o* having a star-shaped cross section. It should be noted that the irregularly shaped elastically deforming part 120*o* is preferably changed into a shape so that a clearance is produced between the elastically deforming part 120*o* and the wall surface of the pharynx when a water soluble holding part dissolves in the pharynx and the elastically deforming part 120*o* is increased in its diameter. Further, the elastically deforming part 120*o* may be made of a material having superior air permeability. It should be noted that the nasal cavity insertion device 100*o* is reduced in its diameter when the elastically deforming part 120*k* is compressed and deformed by the water soluble holding part (not shown in the figure).

Figure 25:
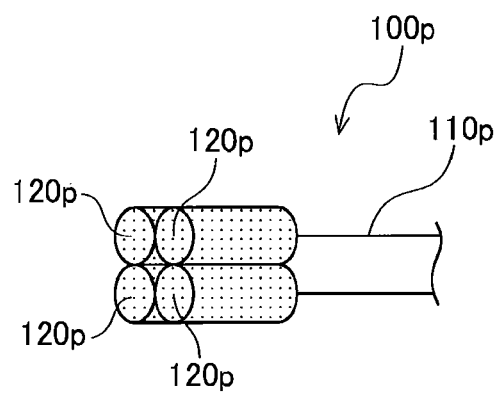
FIG. 25 is a perspective view of a nasal cavity insertion device according to a modification (P).

(P) In the nasal cavity insertion device 100, 200 according to the aforementioned embodiments, the examples have been explained that the elastically deforming parts 120, 220 made of silicone rubber are provided. However, the present invention is not limited to the configurations, and as shown in FIG. 25, elastically deforming parts 120*p* made of a form material with air permeability. In other words, a nasal cavity insertion device 100*p* according to the present modification shown in FIG. 25 includes a main body part 110*p* and the elastically deforming parts 120*p* made of the foam material with air permeability. It should be noted that the following materials are exemplified as the foam material: natural rubber (NR) sponge, isoprene rubber (IR) sponge, styrenebutadiene rubber (SBR) sponge, chloroprene rubber (CR) sponge, acrylonitrilebutadiene rubber (NBR) sponge, ethylenepropylenediene monomer rubber (EPDM) sponge and silicone rubber sponge. It should be noted that the main body part 110*p* of the present modification is not particularly limited and may be either of the tubes shown in the first and second embodiments, the main body part 110*h* as a wire rod (wire) shown in the modification (H), the main body part 110*n*' formed by a coil spring shown in the modification (N) or a main body part 110*r* having a slit 111*r* according to a modification (R) to be described.

Figure 26:
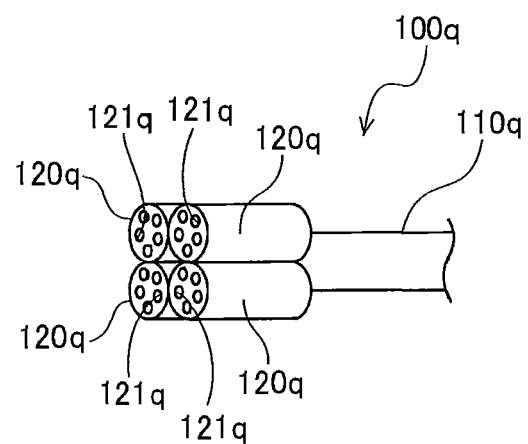
FIG. 26 is a perspective view of a nasal cavity insertion device according to a modification (Q).

(Q) In the nasal cavity insertion device 100, 200 according to the aforementioned embodiments, the examples have been explained that the tubular elastically deforming parts 120, 220 are provided. However, the present invention is not limited to the configurations, and as shown in FIG. 26, elastically deforming parts 120*q* formed by multi-lumen tubes may be provided. In other words, a nasal cavity insertion device 100*q* according to the present modification shown in FIG. 26 includes a main body part 110*q* and the elastically deforming parts 120*q*, each of which is formed by a multi-lumen tube and includes a plurality of apertures 121*q* penetrating therethrough in the longitudinal direction. It should be noted that the main body part 110*q* of the present modification is not particularly limited, and may be either of the tubes shown in the first and second embodiments, the main body part 110*h* as a wire rod (wire) shown in the modification (H), the main body part 110*n*' formed by a coil spring shown in the modification (N) or the main body part 110*r* having the slit 111*r* according to the modification (R) to be described.

Figure 27:
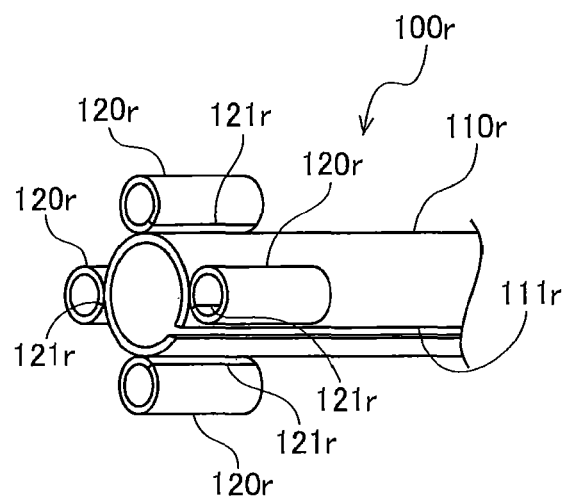
FIG. 27 is a perspective view of a nasal cavity insertion device according to a modification (R).

(R) In the nasal cavity insertion device 100, 200 according to the aforementioned embodiments, the examples have been explained that the tubular main body part 110, 210 is provided. However, the present invention is not limited to the configurations, and as shown in FIG. 27, the tubular main body part 110*r* in which the slit 111*r* is formed in the longitudinal direction may be applied. In other words, a nasal cavity insertion device 100*r* according to the present modification shown in FIG. 27 includes: the main body part 110*r* in which the slit 111*r* is formed in the longitudinal direction; and four tubular elastically deforming parts 120*r*. The slit 111*r* is formed across the entire length of the main body part 110*r*. Accordingly, the main body part 110*r* can be developed in a sheet shape. Thus, reduction in diameter is enabled by rolling up the sheet-shaped main body part 110*r*. It should be noted that the number of the elastically deforming parts 120*r* is not limited to four, and the shape thereof is not limited to a tubular shape. In other words, not only the tubular elastically deforming parts 120, 220 according to the first and second embodiments but also the elastically deforming parts of the other modifications may be used as the elastically deforming parts 120*r*. Further, the main body part 110*r* and the elastically deforming parts 120*r* can be further reduced in their diameters by further forming a slit 121*r* in each elastically deforming part 120*r*. It should be noted that the aforementioned slit 111*r* formed in the main body part 110*r* is not necessarily formed across the entire length of the main body part 110*r*, and may be formed from the tip to an intermediate portion of the main body part 110*r*. Further, the number of the slit 111*r* may be plural. It should be noted that in forming multiple slits 111*r* in the main body part 110*r*, the number of the slits 111*r* formed across the entire length of the main body part 110*r* is less than or equal to one for preventing the main body part 110*r* from being divided into a plurality of sections.

Figure 28:
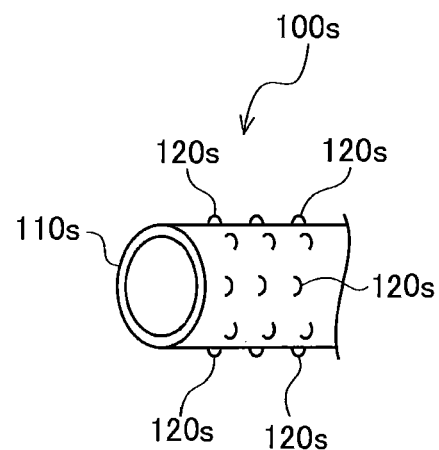
FIG. 28 is a perspective view of a nasal cavity insertion device according to a modification (S).
Figure 29:
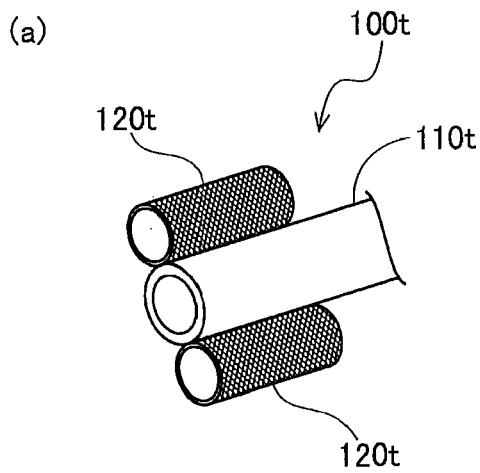
FIG. 29 is a perspective view of a nasal cavity insertion device according to a modification (T).
Figure 29:
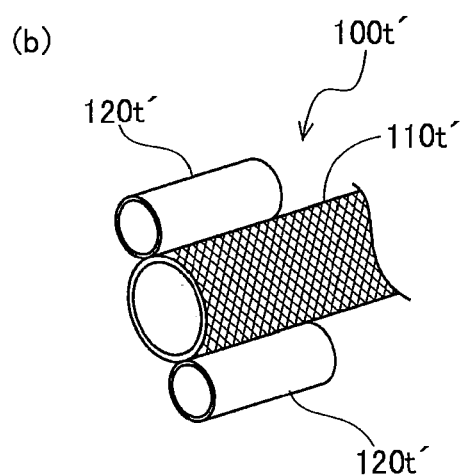
Figure 29:
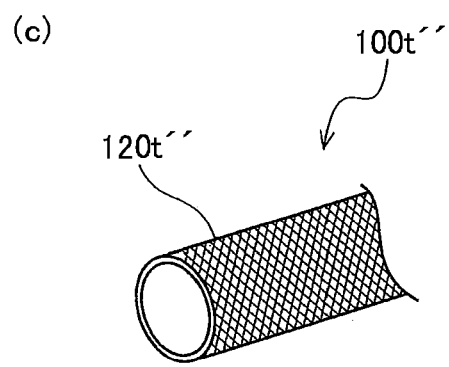

(S) In the nasal cavity insertion device 100, 200 according to the aforementioned embodiments, the examples have been explained that the tubular elastically deforming parts 120, 200 are provided. However, the present invention is not limited to the configurations, and as shown in FIG. 28, elastically deformable convex-shaped elastically deforming parts 120s may be disposed on the outer peripheral surface of the tubular main body part 110s. In other words, a nasal cavity insertion device 100s according to the present modification shown in FIG. 28 includes a tubular main body part 110s and a plurality of convex-shaped elastically deforming parts 120s formed on the outer peripheral surface of the main body part 110s. It should be noted that the nasal cavity insertion device 100s may be reduced in its diameter while the convex-shaped elastically deforming parts 120s are held in a concave state by a water soluble holding part (not shown in the figure). Alternatively, as shown in the modification (R), the nasal cavity insertion device 100s may be reduced in its diameter by forming a slit in the main body part 110s and rolling up the main body part 110s developed in a plate shape.

(T) In the nasal cavity insertion device 100, 200 according to the aforementioned embodiments, the examples have been explained that the elastically deforming parts 120, 220 formed by tubes made of silicone rubber are provided. However, the present invention is not limited to the configurations, and as shown in FIG. 29(a), each elastically deforming part 120t may be a net body formed by weaving a wire rod made of metal or resin. In other words, a nasal cavity insertion device 100t according to the present modification shown in FIG. 29(a) includes a main body part 110t and the elastically deforming parts 120t respectively formed by the net body in a tubular shape.

Alternatively, as shown in FIG. 29(b), a nasal cavity insertion device 100t' according to the present modification may be configured to include a main body part 110t' formed by a net body in a tubular shape and elastically deforming parts 120t' disposed on the outer periphery of the main body part 110t'.

Yet alternatively, as shown in FIG. 29(c), a nasal cavity insertion device 100t" according to the present modification may be configured to include an elastically deforming part 120t' formed by a net body in a tubular shape without including a main body part as an element.

The aforementioned elastically deforming parts 120t and 120t" and the main body part 110t', respectively formed by a net body, are reduced in their diameters when external force is applied thereto. The elastically deforming parts 120t and 120t" and the main body part 110t', which are reduced in their diameters, are held by a water soluble holding part (not shown in the figures).

Figure 30:
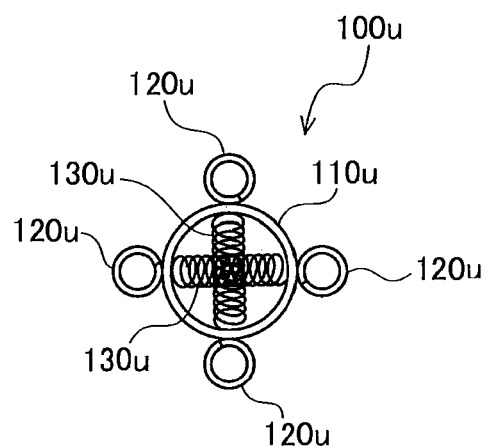
FIG. 30 is a front view of a nasal cavity insertion device according to a modification (U).

(U) In the nasal cavity insertion device 100, 200 according to the aforementioned embodiments, the tubular main body part 110 has a hollow space in its inside. However, the present invention is not limited to the configurations, and as shown in FIG. 30, a main body part 110u may accommodate springs 130u in the hollow space thereof. In other words, a nasal cavity insertion device 100u according to the present modification shown in FIG. 30 includes a tubular main body part 110u, elastically deforming parts 120u disposed on the outer peripheral surface of the main body part 110u, and the springs 130u disposed in the hollow space formed within the main body part 110u. Accordingly, a predetermined restoring force can be applied to the main body part 110u when a water soluble holding part, holding the elastically deforming parts 120u and the main body part 110u in a diameter reduced state, dissolves in the pharynx. It should be noted that the springs 130u may be disposed in the hollow spaces within the tubular elastically deforming parts 120u as well as in the hollow space within the main body part 110u. It should be noted that the nasal cavity insertion device 100u may be reduced in its diameter by causing a water soluble holding part (not shown in the figure) to hold the elastically deforming parts 120u while the inner peripheral surface of each elastically deforming part 120u makes contact with the outer peripheral surface of the main body, or alternatively, hold the main body part 110u in a compressed state against the urging force of the springs 130u.

Figure 31:
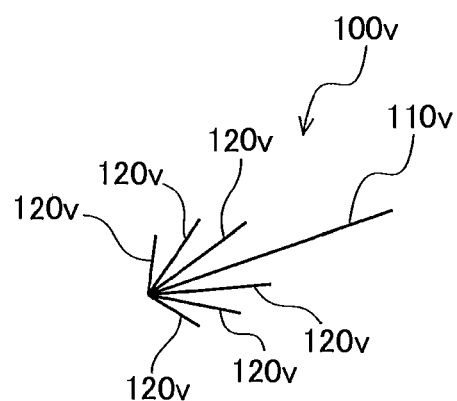
FIG. 31 is a perspective view of a nasal cavity insertion device according to a modification (V).

(V) In the nasal cavity insertion device 100, 200 according to the aforementioned embodiments, the examples have been explained that the tubular main body part 110, 210 is provided with the tubular elastically deforming parts 120, 220. However, the present invention is not limited to the configurations, and as shown in FIG. 31, a main body part 110v may be provided with elastically deforming parts 120v in a radial shape so that an umbrella frame-like shape can be entirely formed. In other words, a nasal cavity insertion device 100v according to the present modification shown in FIG. 31 includes the main body part 110v and the multiple elastically deforming parts 120v that are coupled to the tip of the main body part 110v while being radially disposed with respect to the main body part 110v. It should be noted that the nasal cavity insertion device 100v is reduced in its diameter while the multiple elastically deforming parts 120k are held and bundled together with the main body part 110v by a water soluble holding part (not shown in the figure). It should be noted that in the nasal cavity insertion device 100v according to the present modification, the elastically deforming parts 120v are coupled to the tip of the main body part 110v. However, the attachment position of the elastically deforming parts 120v may not be the tip of the main body part 110v. In other words, the elastically deforming parts 120v may be attached to a position displaced at a predetermined distance from the tip of the main body part 110v towards the base end thereof.

Figure 32:
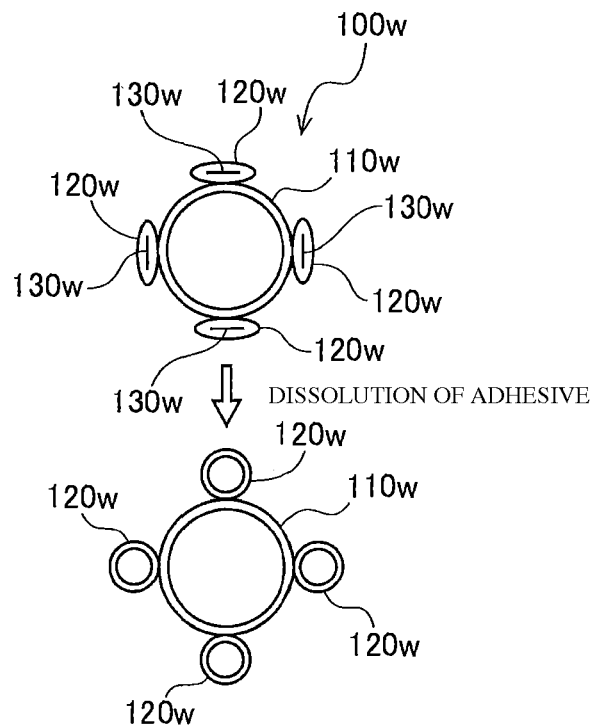
FIG. 32 is a front view of a nasal cavity insertion device according to a modification (W).

(W) In the nasal cavity insertion device 100, 200 according to the aforementioned embodiments, the examples of reducing the diameters of the elastically deforming parts 120, 220 by means of the water soluble holding part (the wafer film 130, the gelatin organizer 230) have been explained. However, the present invention is not limited to the configurations, and as shown in FIG. 32, each elastically deforming part 120w may be reduced in its diameter while being formed in a flattened state by means of an adhesive 130w as a water soluble holding part applied to the inside of each elastically deforming part 120w. Specifically, each elastically deforming part 120w is compressed for reducing its diameter. In other words, a nasal cavity insertion device 100w according to the present modification shown in FIG. 32 includes a main body part 110w, the tubular elastically deforming parts 120w attached to the outer peripheral surface of the main body part 110w, and an adhesive (water soluble holding part) 130w that is applied to the inside of each elastically deforming part 120w and holds each elastically deforming part 120w in a diameter reduced state. According to the aforementioned configuration, the adhesive (water soluble holding part) 130w dissolves in the pharynx and each elastically deforming part 120w is thereby increased in its diameter. It should be herein noted that each elastically deforming part 120w, reduced in its diameter in a flattened state, is maintained in the flattened state by means of the adhesive force of the adhesive 130w in the inside thereof, and is accordingly reduced in its diameter. However, the adhesive (water soluble holding part) 130w may be applied to the inside of the tubular main body part 110w so that the main body part 110w can be reduced in its diameter by means of the adhesive 130w. It should be noted that the main body part 110w may be compressed for reducing its diameter, or alternatively, may be pulled in the longitudinal direction thereof for reducing its diameter.

Figure 33:
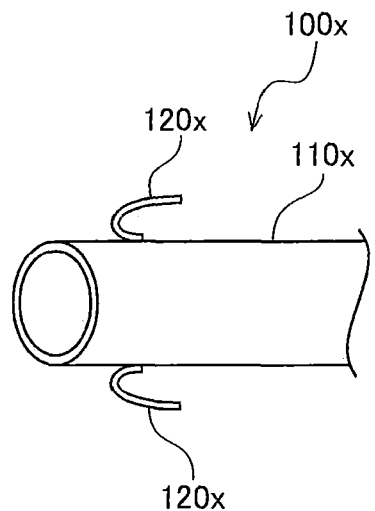
FIG. 33 is a perspective view of a nasal cavity insertion device according to a modification (X).
Figure 34:
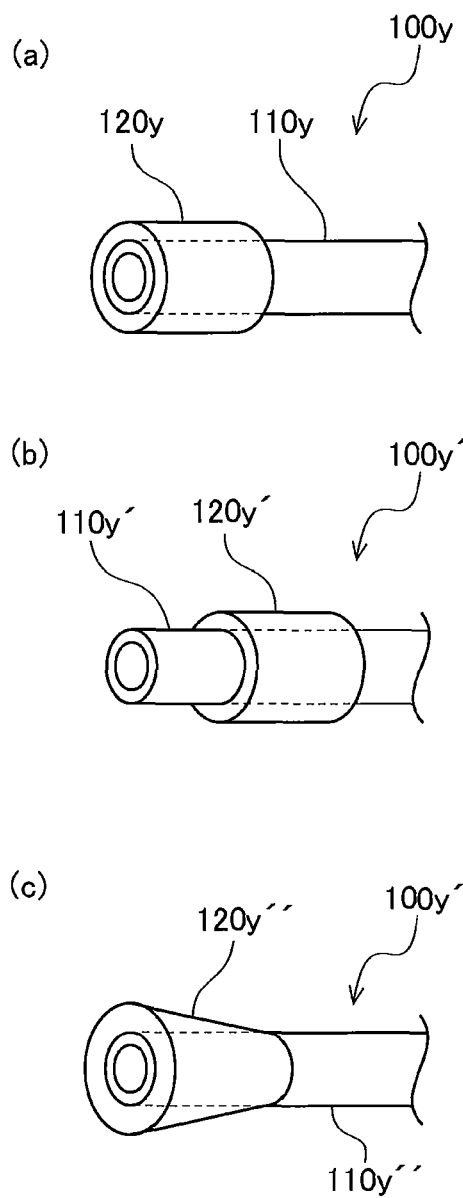
FIG. 34 is a perspective view of a nasal cavity insertion device according to a modification (Y).

(X) In the nasal cavity insertion device 100, 200 according to the aforementioned embodiments, the examples of providing the tubular elastically deforming parts 120, 220 have been explained. However, the present invention is not limited to the configurations, and as shown in FIG. 33, hook-shaped elastically deforming parts 120x may be provided. In other words, a nasal cavity insertion device 100x according to the present modification shown in FIG. 33 includes a main body part 110x and the hook-shaped elastically deforming parts 120x attached to the outer peripheral surface of the main body part 110x. Each elastically deforming part 120x is extended to the tip side of the main body part 110x from its portion connected to the main body part 110x, and is then folded back and extended towards the base end of the main body part 110x. It should be noted that the nasal cavity insertion device 100x is reduced in its diameter while the hook-shaped elastically deforming parts 120x are pressed towards the main body part 110v by means of a water soluble holding part (not shown in the figure).

(Y) In the nasal cavity insertion device 100, 200 according to the aforementioned embodiments, the examples of disposing the four elastically deforming parts 120, 220 on the outer peripheral surface of the main body part 110 have been explained. However, the present invention is not limited to the configurations, and as shown in FIGS. 34(a), 34(b) and 34(c), an elastically deforming part 120y, 120y', 120y'' may be formed while being wound about the outer peripheral surface of a main body part 110y, 110y', 110y''. A nasal cavity insertion device 100y according to the modification shown in FIG. 34(a) includes the tubular main body part 110y and the elastically deforming part 120y formed while being wound about the outer peripheral surface of the main body part 110y at the tip position of the main body part 110y. Further, a nasal cavity insertion device 100y' according to the modification shown in FIG. 34(b) includes the tubular main body part 110y' and the elastically deforming part 120y' formed while being wound about the outer peripheral surface of the main body part 110y' at a position displaced from the tip end toward the base end of the main body part 110y'. Yet further, the nasal cavity insertion device 100y'' according to the modification shown in FIG. 34(c) includes the tubular main body part 110y'' and the elastically deforming part 120y'' that is formed in a circular truncated cone shape while being wound about the outer peripheral surface of the main body part 110y''.

It should be noted that the nasal cavity insertion device 100y, 100y', 100y'' is reduced in its diameter while the elastically deforming part 120y, 120y'', 120y'' is compressed and deformed by a water soluble holding part (not shown in the figures). Further, the nasal cavity insertion device 100y may be reduced in its diameter while the tubular main body part 110y, 110y', 110y'' is compressed and deformed by a water soluble holding part (not shown in the figures).

(Z) Further, in the nasal cavity insertion device 100, 200 according to the aforementioned embodiments, the example of winding the wafer film 130 about the elastically deforming parts 120 and the example of attaching the gelatin organizer 230 (the cylindrical holders 231 to 233 and the holder 234 having a dome-shaped tip portion) to the elastically deforming parts 220. The water soluble holding parts may not be limited to the wafer film 130 and the gelatin organizer 230 as described above, and alternatively, may be a thread ring and a water soluble holding part formed by a net body.

The nasal cavity insertion device according to the present invention is characterized in that the pharynx can be sufficiently expanded, it takes less time to set the device, and further, a user is not forced to take time and effort of an operation. Therefore, the present nasal cavity insertion device is useful as a new type nasal cavity insertion device.

The invention claimed is:

1. A nasal cavity insertion device, comprising:
   a main body part having a tube shape, the main body part including a ventilation channel that is in communication with an outside and allows passage of air; and
   a plurality of elastically deforming parts disposed at an end portion of the main body part, the plurality of elastically deforming parts being configured to expand a pharynx, wherein each of the plurality of elastically deforming parts separately extend away from the main body part when the end portion of the main body part is inserted into a nasal passage,
   wherein the plurality of elastically deforming parts are intermittently disposed on an outer peripheral surface of the tube shape of the main body part along a circumferential direction of the tube shape of the main body part, and
   each of the plurality of elastically deforming parts has at least one of the shapes of a columnar shape, a cylindrical shape, a plate shape, a multi-lumen shape and a coil spring shape.

2. The nasal cavity insertion device according to claim 1, further comprising:
   a water soluble holding part engaging the plurality of elastically deforming parts to hold the plurality of elastically deforming parts in a diameter reduced state.

3. The nasal cavity insertion device according to claim 2, wherein the plurality of elastically deforming parts are cut out only at a portion thereof across an entire length thereof.

4. The nasal cavity insertion device according to claim 2, wherein the water soluble holding part is either a water soluble thin film made from wafer, gelatin or polysaccharide, or a tubular water soluble organizer made from wafer, gelatin or polysaccharide.

5. The nasal cavity insertion device according to claim 2, wherein a portion, covering tips of the plurality of elastically deforming parts, of the water soluble holding part is formed in a dome shape with a convex surface on a tip side thereof.

6. The nasal cavity insertion device according to claim 1, wherein each of the plurality of elastically deforming parts has a base end side and a tip end side in a longitudinal direction of the main body part and a base end side portion slanted towards the main body part from the tip end side to the base end side.

7. The nasal cavity insertion device according to claim 1, wherein the main body part has slit formed in a longitudinal direction.

8. The nasal cavity insertion device according to claim 1, wherein a hardness of the main body part is greater than a hardness of each of the plurality of elastically deforming parts.

* * * * *